United States Patent
Louie et al.

(10) Patent No.: US 8,584,941 B2
(45) Date of Patent: Nov. 19, 2013

(54) PHARMACY TRACKING SYSTEM WITH AUTOMATICALLY-ENTERED CUSTOMER TRANSACTION INFORMATION

(75) Inventors: Shelton Louie, Vancouver, WA (US); Stephen A. Garrett, Vancouver, WA (US); Joseph Intile, Tualatin, OR (US)

(73) Assignee: GSL Solutions, Inc., Vancouver, WA (US)

( * ) Notice: Subject to any disclaimer, the term of this patent is extended or adjusted under 35 U.S.C. 154(b) by 0 days.

(21) Appl. No.: 13/282,196

(22) Filed: Oct. 26, 2011

(65) Prior Publication Data

US 2012/0041781 A1 Feb. 16, 2012

Related U.S. Application Data

(63) Continuation of application No. 13/050,308, filed on Mar. 17, 2011, and a continuation-in-part of application No. 12/268,389, filed on Nov. 10, 2008, now abandoned, which is a continuation of application No. 11/213,321, filed on Aug. 25, 2005, now Pat. No. 7,448,544, and a continuation-in-part of application No. 09/715,439, filed on Nov. 16, 2000, now Pat. No. 7,672,859, said application No. 13/050,308 is a continuation-in-part of application No. 13/027,075, filed on Feb. 14, 2011, which is a continuation of application No. 10/223,308, filed on Aug. 18, 2002, now Pat. No. 7,887,146.

(60) Provisional application No. 61/444,062, filed on Feb. 17, 2011, provisional application No. 60/605,274, filed on Aug. 26, 2004, provisional application No. 60/313,305, filed on Aug. 18, 2001.

(51) Int. Cl.
*G06F 19/00* (2011.01)

(52) U.S. Cl.
USPC .......................................................... 235/385

(58) Field of Classification Search
USPC ................................ 235/375, 385; 705/22, 28
See application file for complete search history.

(56) References Cited

U.S. PATENT DOCUMENTS

| 404,458 A | 6/1889 | Woodruff |
| 541,111 A | 6/1895 | McDonald |
| 827,649 A | 7/1906 | Murphy |
| 1,236,324 A | 8/1917 | Leonard |
| 1,592,497 A | 7/1926 | Mays |
| 1,750,291 A | 3/1930 | Whetstone |
| 1,993,477 A | 3/1935 | Glenn et al. |

(Continued)

FOREIGN PATENT DOCUMENTS

| EP | 0 899 677 | 3/1999 |
| EP | 1 049 042 | 11/2000 |

OTHER PUBLICATIONS

Office action dated Feb. 15, 2012, U.S. Appl. No. 12/715,256, filed Mar. 1, 2010.

(Continued)

*Primary Examiner* — Jamara Franklin
(74) *Attorney, Agent, or Firm* — Lane Powell PC

(57) ABSTRACT

A method of conducting a transaction involving transfer of a filled prescription order from a pharmacy to a customer. The method includes detecting that the filled prescription order is available for transfer from the pharmacy to the customer. Upon detecting that the filled prescription order is available for transfer from the pharmacy to the customer, the method automatically completes at least one process for facilitating the transfer of the filled prescription order to the customer.

25 Claims, 24 Drawing Sheets

(56) References Cited

U.S. PATENT DOCUMENTS

| | | |
|---|---|---|
| 2,174,068 A | 9/1939 | Citron |
| 2,962,335 A | 11/1960 | Benson |
| 3,167,873 A | 2/1965 | Toms |
| 3,172,711 A | 3/1965 | Gillotte |
| 3,744,867 A | 7/1973 | Shaw |
| 3,798,810 A | 3/1974 | Brisson et al. |
| 3,844,416 A | 10/1974 | Potter |
| 3,865,447 A | 2/1975 | Patterson |
| 3,942,851 A | 3/1976 | Kaplan |
| 3,970,010 A | 7/1976 | Cantley |
| 4,210,802 A | 7/1980 | Sakai |
| 4,653,818 A | 3/1987 | DeBruyn |
| 4,688,026 A | 8/1987 | Scribner et al. |
| 4,737,910 A | 4/1988 | Kimbrow |
| 4,746,830 A | 5/1988 | Holland |
| 4,766,542 A | 8/1988 | Pilarczyk |
| 4,793,495 A | 12/1988 | Preu |
| 4,993,558 A | 2/1991 | Assael |
| 5,047,948 A | 9/1991 | Turner |
| 5,079,006 A | 1/1992 | Urquhart |
| 5,160,048 A | 11/1992 | Leyden et al. |
| 5,208,762 A | 5/1993 | Charhut et al. |
| 5,231,273 A | 7/1993 | Caswell et al. |
| 5,245,163 A | 9/1993 | Bar-Yehuda |
| 5,328,784 A | 7/1994 | Fukuda |
| 5,346,297 A | 9/1994 | Colson et al. |
| 5,389,919 A | 2/1995 | Warren et al. |
| 5,434,775 A | 7/1995 | Sims et al. |
| 5,481,546 A | 1/1996 | Dinkins |
| 5,495,250 A | 2/1996 | Ghaem et al. |
| 5,593,267 A | 1/1997 | McDonald et al. |
| 5,595,356 A | 1/1997 | Kewin |
| 5,597,995 A | 1/1997 | Williams et al. |
| 5,640,002 A | 6/1997 | Ruppert et al. |
| 5,646,389 A | 7/1997 | Bravman et al. |
| 5,646,592 A | 7/1997 | Tuttle |
| 5,689,238 A | 11/1997 | Cannon et al. |
| 5,700,998 A | 12/1997 | Palti |
| 5,771,657 A | 6/1998 | Lasher et al. |
| 5,794,213 A | 8/1998 | Markman |
| 5,797,515 A | 8/1998 | Liff et al. |
| 5,798,693 A | 8/1998 | Engellenner |
| 5,805,456 A | 9/1998 | Higham et al. |
| 5,838,253 A | 11/1998 | Wurz et al. |
| 5,845,264 A | 12/1998 | Nellhaus |
| 5,907,493 A | 5/1999 | Boyer et al. |
| 5,926,093 A | 7/1999 | Bowers et al. |
| 5,936,527 A | 8/1999 | Isaacman et al. |
| 5,963,132 A | 10/1999 | Yoakum |
| 5,974,393 A | 10/1999 | McCullough et al. |
| 5,996,889 A | 12/1999 | Fuchs et al. |
| 6,008,727 A | 12/1999 | Want et al. |
| 6,021,392 A | 2/2000 | Lester et al. |
| 6,057,756 A | 5/2000 | Engellenner |
| 6,057,764 A | 5/2000 | Williams |
| 6,098,892 A | 8/2000 | Peoples |
| 6,116,505 A | 9/2000 | Withrow |
| 6,150,942 A | 11/2000 | O'Brien |
| 6,170,746 B1 | 1/2001 | Brook et al. |
| 6,202,923 B1 | 3/2001 | Boyer et al. |
| 6,209,978 B1 | 4/2001 | Khan |
| 6,219,587 B1 | 4/2001 | Ahlin et al. |
| 6,223,137 B1 | 4/2001 | McCay et al. |
| 6,232,876 B1 | 5/2001 | Maloney |
| 6,245,057 B1 | 6/2001 | Sieben et al. |
| 6,249,212 B1 | 6/2001 | Beigel et al. |
| 6,259,654 B1 | 7/2001 | de la Huerga |
| 6,294,999 B1 | 9/2001 | Yarin et al. |
| 6,318,536 B1 | 11/2001 | Korman et al. |
| 6,324,522 B2 | 11/2001 | Peterson et al. |
| 6,339,732 B1 | 1/2002 | Phoon et al. |
| 6,354,493 B1 | 3/2002 | Mon |
| 6,357,662 B1 | 3/2002 | Helton et al. |
| 6,366,206 B1 | 4/2002 | Ishikawa et al. |
| 6,366,220 B1 | 4/2002 | Elliott |
| 6,380,858 B1 | 4/2002 | Yarin et al. |
| 6,392,544 B1 | 5/2002 | Collins et al. |
| 6,393,339 B1 | 5/2002 | Yeadon |
| 6,415,295 B1 | 7/2002 | Feinberg |
| 6,415,978 B1 | 7/2002 | McAllister |
| 6,430,268 B1 | 8/2002 | Petite |
| 6,440,069 B1 | 8/2002 | Raymond et al. |
| 6,448,886 B2 | 9/2002 | Garber et al. |
| 6,450,406 B2 | 9/2002 | Brown |
| 6,464,142 B1 | 10/2002 | Denenberg et al. |
| 6,496,806 B1 | 12/2002 | Horwitz et al. |
| 6,502,005 B1 | 12/2002 | Wrubel et al. |
| 6,522,945 B2 | 2/2003 | Sleep et al. |
| 6,529,786 B1 | 3/2003 | Sim |
| 6,557,758 B1 | 5/2003 | Monico |
| 6,564,121 B1 | 5/2003 | Wallace et al. |
| 6,611,806 B1 | 8/2003 | Harvey |
| 6,648,153 B2 | 11/2003 | Holmes |
| 6,714,121 B1 | 3/2004 | Moore |
| 6,758,403 B1 | 7/2004 | Keys et al. |
| 6,763,996 B2 | 7/2004 | Rakers et al. |
| 6,769,228 B1 | 8/2004 | Mahar |
| 6,877,658 B2 | 4/2005 | Raistrick et al. |
| 6,935,560 B2 | 8/2005 | Andreasson et al. |
| 6,995,675 B2 | 2/2006 | Curkendall et al. |
| 7,142,118 B2 | 11/2006 | Hamilton et al. |
| 7,148,803 B2 | 12/2006 | Bandy et al. |
| 7,158,030 B2 | 1/2007 | Chung |
| 7,175,081 B2 | 2/2007 | Andreasson et al. |
| 7,194,333 B2 | 3/2007 | Shoenfeld |
| 7,289,015 B2 | 10/2007 | Moyer |
| 7,382,263 B2 | 6/2008 | Danowski et al. |
| 7,672,859 B1 | 3/2010 | Louie et al. |
| 7,887,146 B1 | 2/2011 | Louie et al. |
| 2001/0017817 A1 | 8/2001 | de la Huerga |
| 2001/0040512 A1 | 11/2001 | Hines et al. |
| 2002/0132226 A1 | 9/2002 | Nair et al. |
| 2002/0180588 A1 | 12/2002 | Erickson et al. |
| 2003/0086338 A1 | 5/2003 | Sastry et al. |
| 2003/0191430 A1 | 10/2003 | D'Andrea et al. |
| 2003/0200726 A1 | 10/2003 | Rast |
| 2004/0036623 A1 | 2/2004 | Chung |
| 2005/0237201 A1 | 10/2005 | Nedblake |
| 2006/0190628 A1 | 8/2006 | Linton et al. |

OTHER PUBLICATIONS

Office action dated May 10, 2004, U.S. Appl. No. 09/991,530, filed Aug. 18, 2002.
Final Office action dated Feb. 23, 2005, U.S. Appl. No. 09/991,530, filed Aug. 18, 2002.
Office action dated Oct. 13, 2004, U.S. Appl. No. 10/223,336, filed Aug. 18, 2002.
Final Office action dated Jun. 23, 2005, U.S. Appl. No. 10/223,336, filed Aug. 18, 2002.
Office action dated Aug. 15, 2006, U.S. Appl. No. 10/223,336, filed Aug. 18, 2002.
Final Office action dated Apr. 25, 2007, U.S. Appl. No. 10/223,336, filed Aug. 18, 2002.
Office action dated Aug. 1, 2011, U.S. Appl. No. 12/715,256, filed Mar. 1, 2010.
Office action dated May 12, 2009, U.S. Appl. No. 10/928,758, filed Aug. 26, 2004.
Final Office action dated Mar. 16, 2010, U.S. Appl. No. 10/928,758, filed Aug. 26, 2004.
Office action dated Aug. 7, 2008, U.S. Appl. No. 10/928,756, filed Aug. 26, 2004.
Final Office action dated Jun. 18, 2009, U.S. Appl. No. 10/928,756, filed Aug. 26, 2004.
Office action dated Jan. 19, 2010, U.S. Appl. No. 12/268,389, filed Nov. 10, 2008.
Final Office action dated Oct. 4, 2010, U.S. Appl. No. 12/268,389, filed Nov. 10, 2008.
Advisory Action dated May 13, 2010, U.S. Appl. No. 12/268,389, filed Nov. 10, 2008.
Office action dated Dec. 23, 2003, U.S. Appl. No. 10/223,308, filed Aug. 18, 2002.

(56) References Cited

OTHER PUBLICATIONS

Final Office action dated Oct. 8, 2004, U.S. Appl. No. 10/223,308, filed Aug. 18, 2002.
Office action dated Dec. 2, 2005, U.S. Appl. No. 10/223,308, filed Aug. 18, 2002.
Final Office action dated Aug. 25, 2006, U.S. Appl. No. 10/223,308, filed Aug. 18, 2002.
Office action dated Nov. 2, 2007, U.S. Appl. No. 10/223,308, filed Aug. 18, 2002.
Final Office action dated Dec. 24, 2008, U.S. Appl. No. 10/223,308, filed Aug. 18, 2002.
Office action dated Mar. 2, 2010, U.S. Appl. No. 10/223,308, filed Aug. 18, 2002.
Office action dated Jun. 9, 2011, U.S. Appl. No. 12/825,020, filed Jun. 28, 2010.
Office action dated Jun. 11, 2009, U.S. Appl. No. 09/715,439, filed Nov. 16, 2000.
Office action dated Nov. 27, 2007, U.S. Appl. No. 09/715,439, filed Nov. 16, 2000.
Office action dated Nov. 6, 2006, U.S. Appl. No. 09/715,439, filed Nov. 16, 2000.
Office action dated Jan. 12, 2005, U.S. Appl. No. 09/715,439, filed Nov. 16, 2000.
Office action dated Mar. 30, 2004, U.S. Appl. No. 09/715,439, filed Nov. 16, 2000.
Office action dated Sep. 5, 2003, U.S. Appl. No. 09/715,439, filed Nov. 16, 2000.
Office action dated Oct. 21, 2002, U.S. Appl. No. 09/715,439, filed Nov. 16, 2000.
Final Office action dated Sep. 4, 2008, U.S. Appl. No. 09/715,439, filed Nov. 16, 2000.
Final Office action dated Jun. 15, 2007, U.S. Appl. No. 09/715,439, filed Nov. 16, 2000.
Final Office action dated Sep. 21, 2005, U.S. Appl. No. 09/715,439, filed Nov. 16, 2000.
Final Office action dated May 15, 2003, U.S. Appl. No. 09/715,439, filed Nov. 16, 2000.
Final Office action dated Jul. 16, 2004, U.S. Appl. No. 09/829,536, filed Apr. 9, 2001.
Final Office action dated Dec. 28, 2005, U.S. Appl. No. 09/829,536, filed Apr. 9, 2001.
Final Office action dated Dec. 4, 2007, U.S. Appl. No. 09/829,536, filed Apr. 9, 2001.
Office action dated Nov. 12, 2003, U.S. Appl. No. 09/829,536, filed Apr. 9, 2001.
Office action dated Apr. 8, 2005, U.S. Appl. No. 09/829,536, filed Apr. 9, 2001.
Office action dated Apr. 19, 2007, U.S. Appl. No. 09/829,536, filed Apr. 9, 2001.
Office action dated Apr. 28, 2004, U.S. Appl. No. 09/991,249, filed Nov. 16, 2001.
Final Office action dated May 17, 2006, U.S. Appl. No. 09/991,249, filed Nov. 16, 2001.
Office action dated Sep. 8, 2004 U.S. Appl. No. 09/991,529, filed Nov. 16, 2001.
Final Office action dated Feb. 21, 2007, U.S. Appl. No. 09/991,529, filed Nov. 16, 2001.
Office action dated Mar. 13, 2009 U.S. Appl. No. 10/929,110, filed Aug. 26, 2004.
Office action dated Jan. 14, 2008 U.S. Appl. No. 10/928,717, filed Aug. 26, 2004.
Office action dated Apr. 4, 2007, U.S. Appl. No. 11/213,321, filed Aug. 25, 2005.
Office action dated Dec. 17, 2007, U.S. Appl. No. 11/213,321, filed Aug. 25, 2005.
White, Ron, How Computers Work, Millenium Ed., Que Corporation, Sep. 22, 1999.
Derfler, Frank J. et al., How Networks Work, Millenium Ed., Que Corporation, Aug. 23, 2000.
Gralla, Preston, How the Internet Works, Millenium Ed., Que Corporation, Sep. 23, 1999.
Office action dated Aug. 29, 2012, U.S. Appl. No. 13/027,075, filed Feb. 14, 2011.

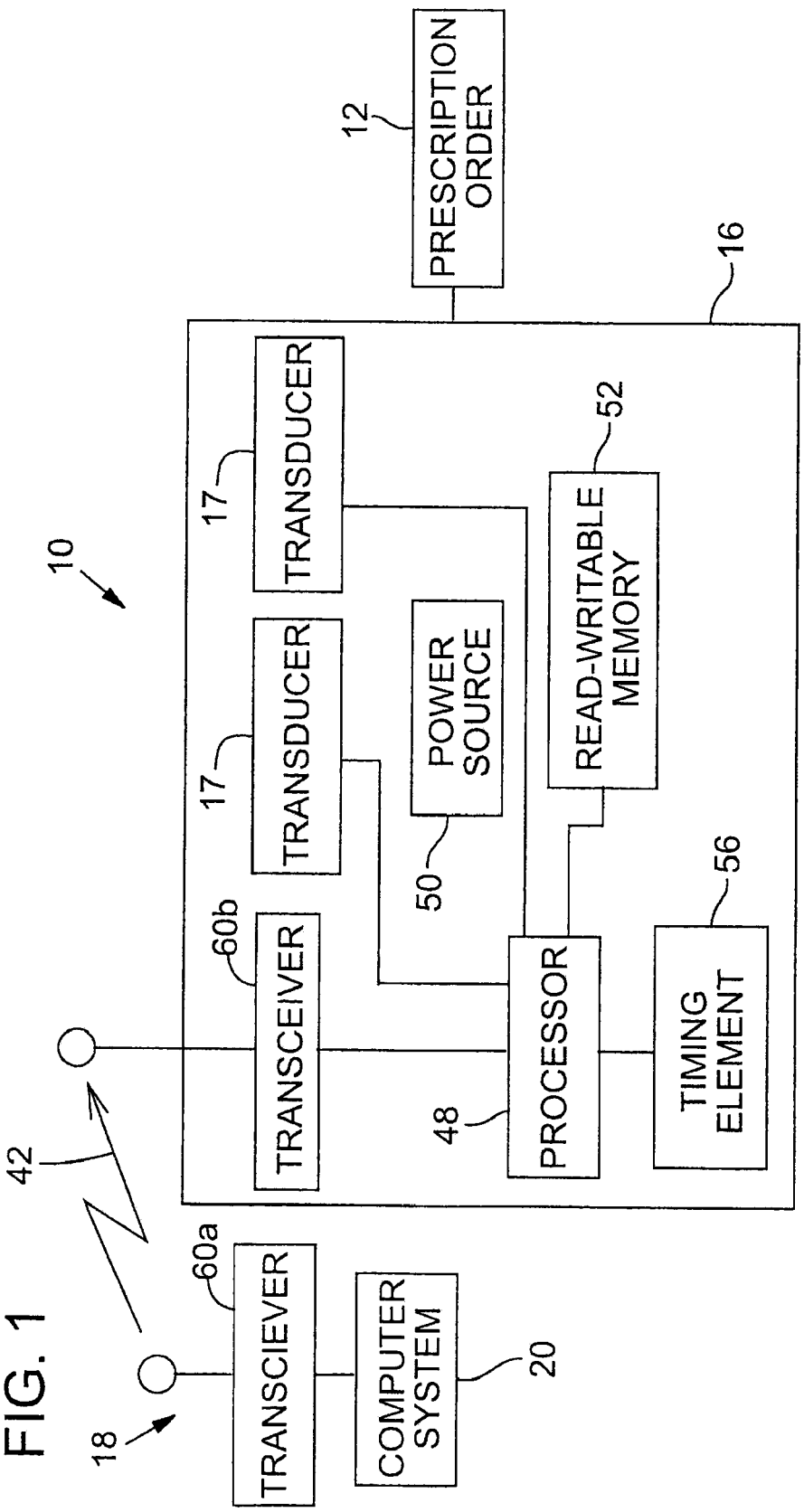

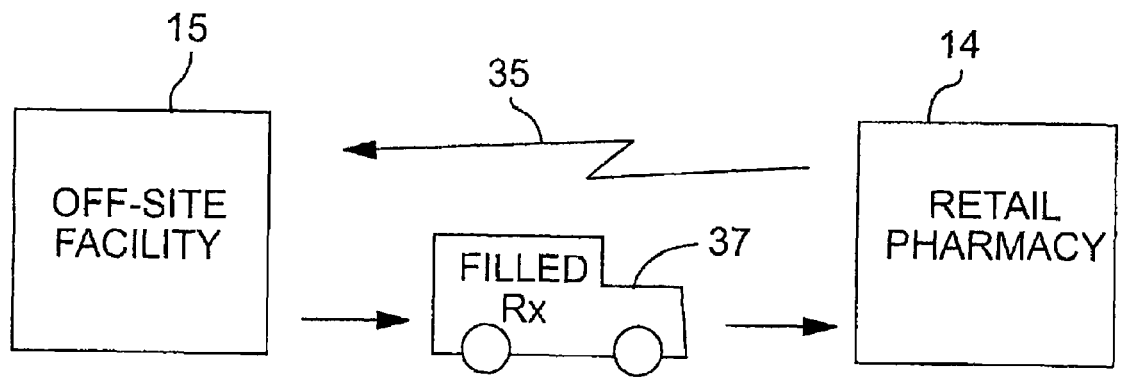
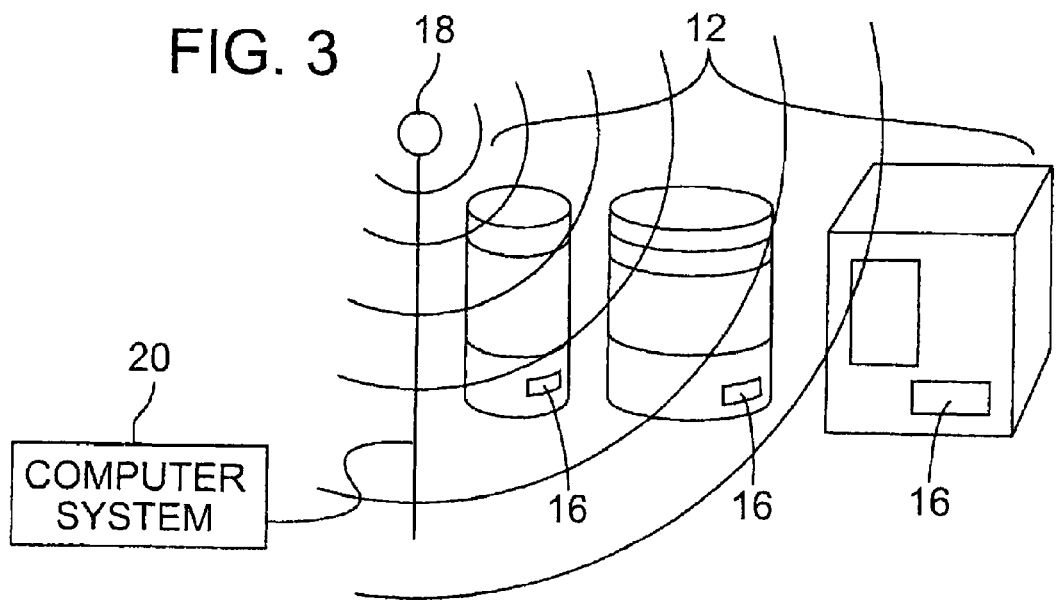

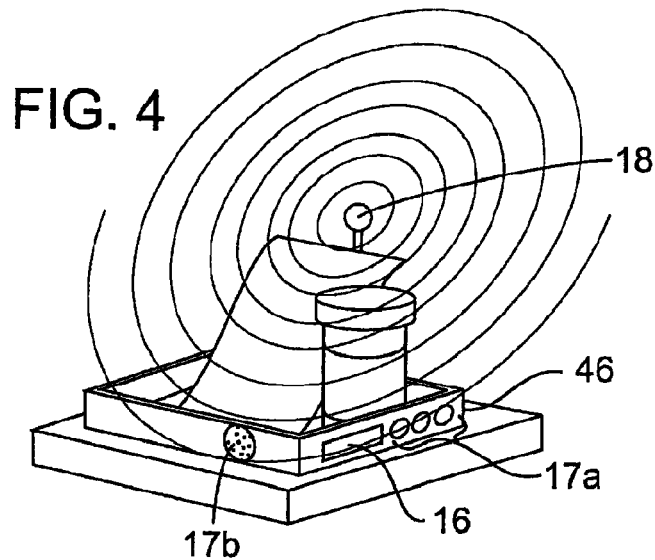
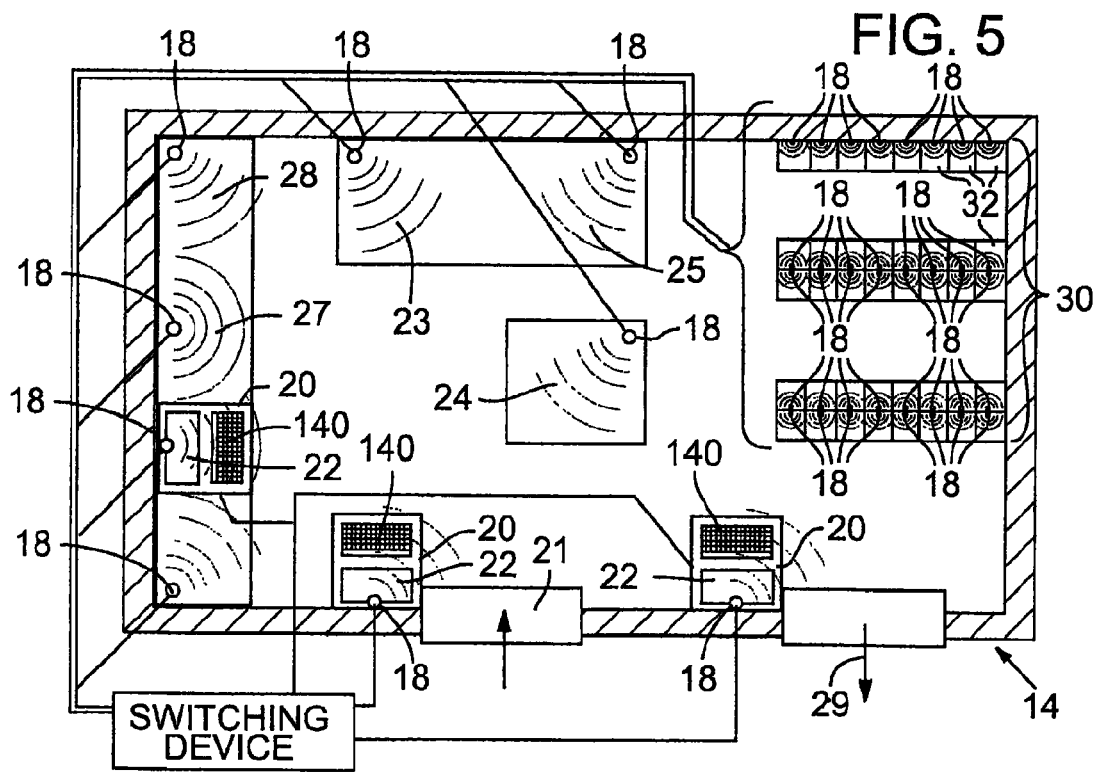

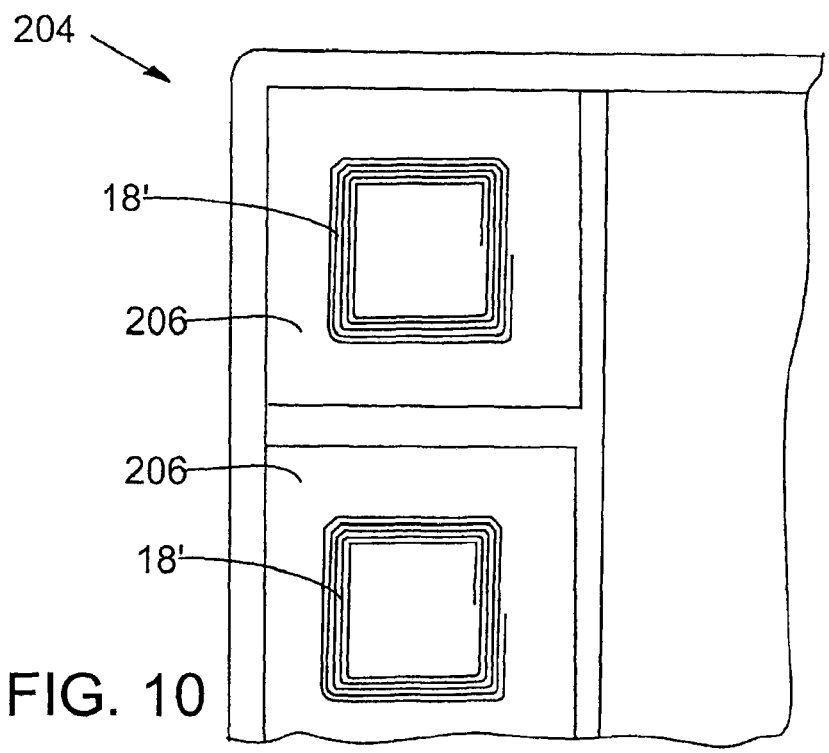
FIG. 10
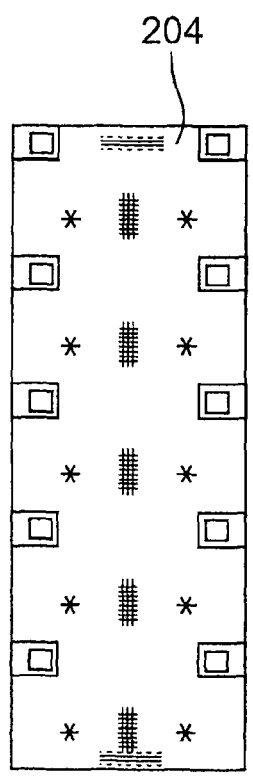  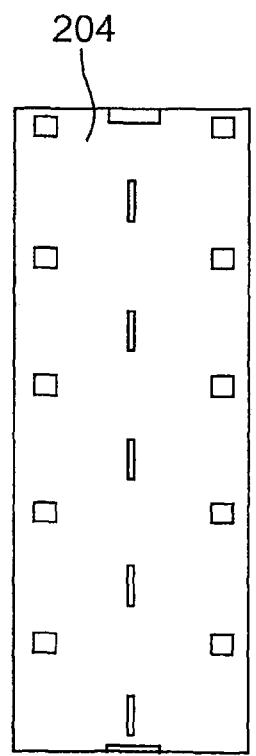
FIG. 11A  FIG. 11B  FIG. 11C

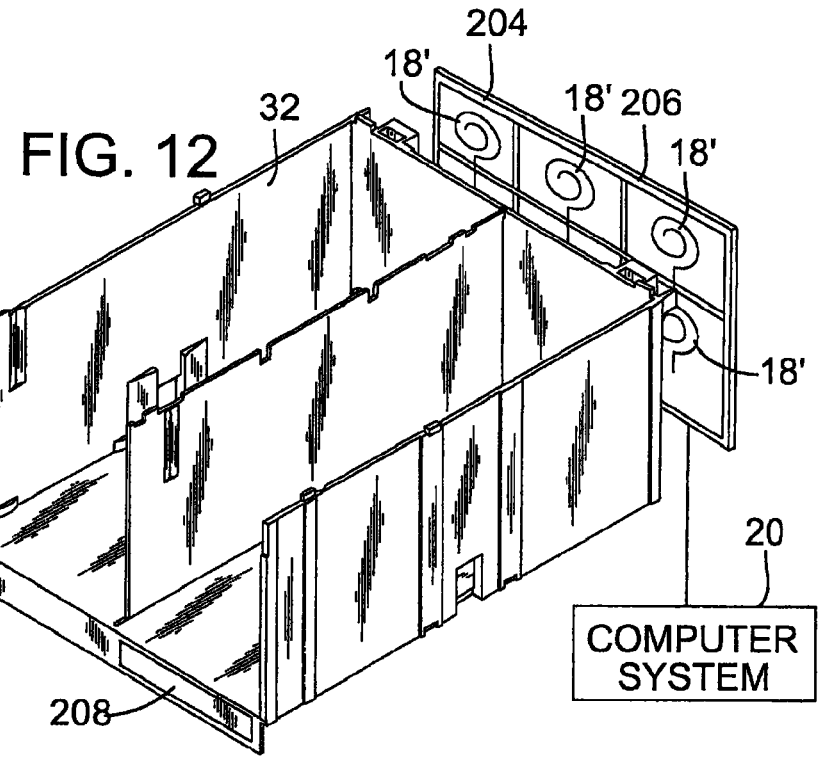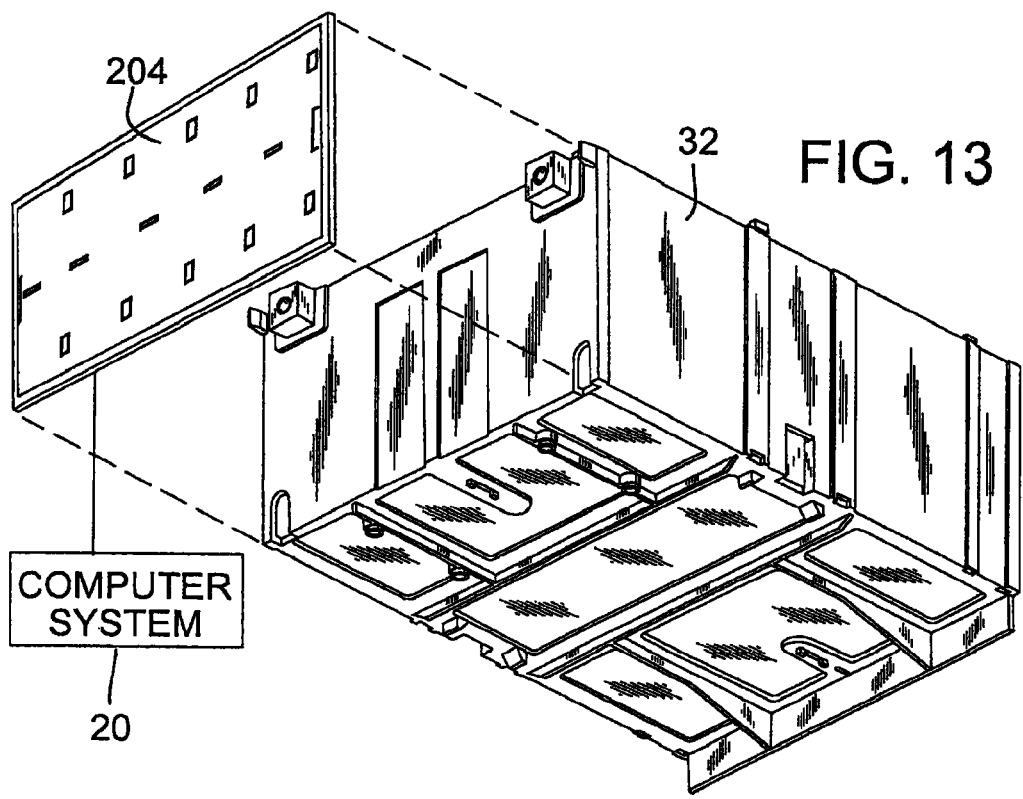

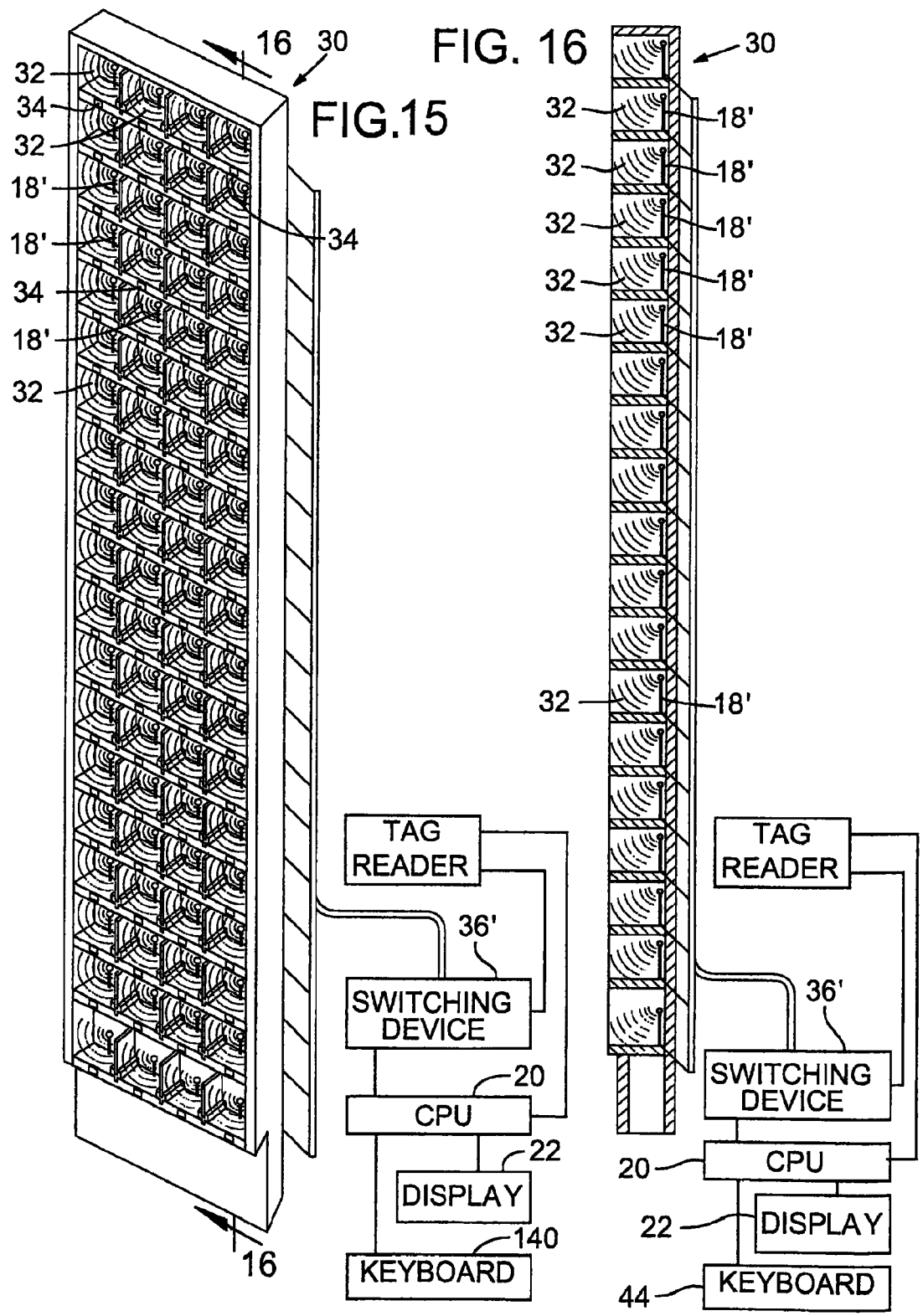

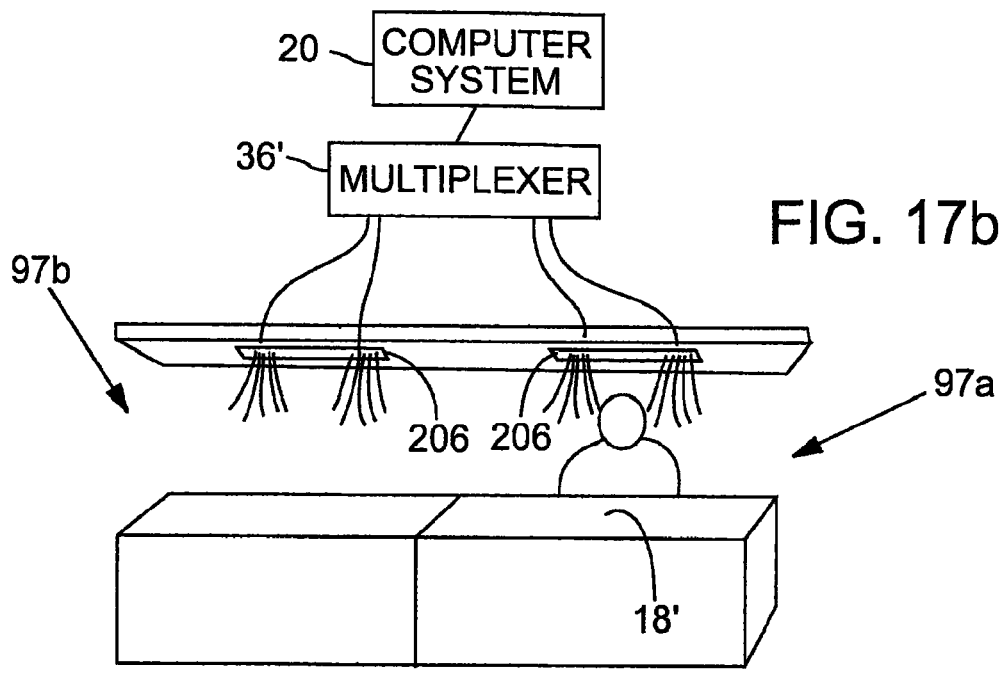
FIG. 17b
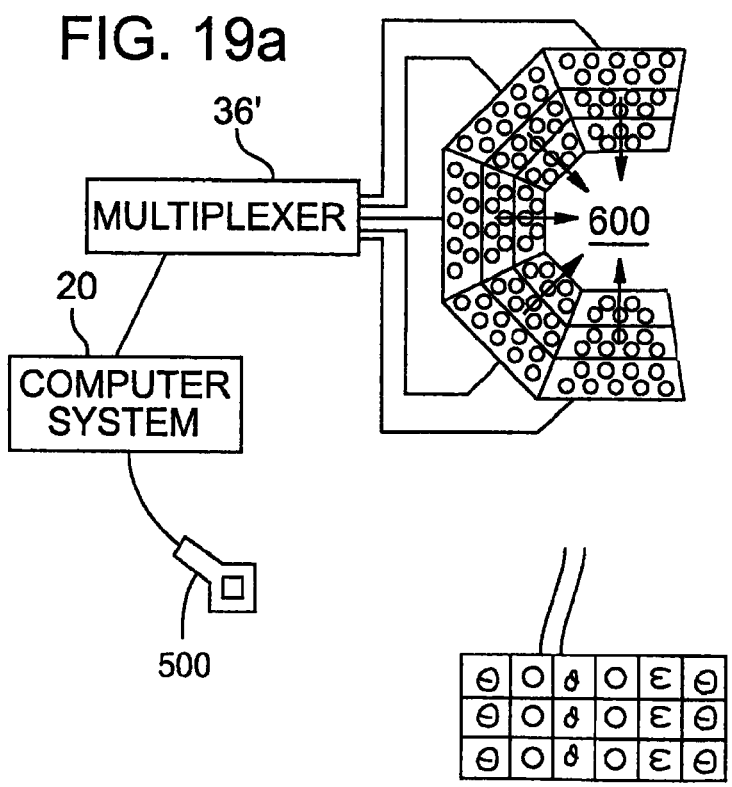
FIG. 19a
FIG. 19b

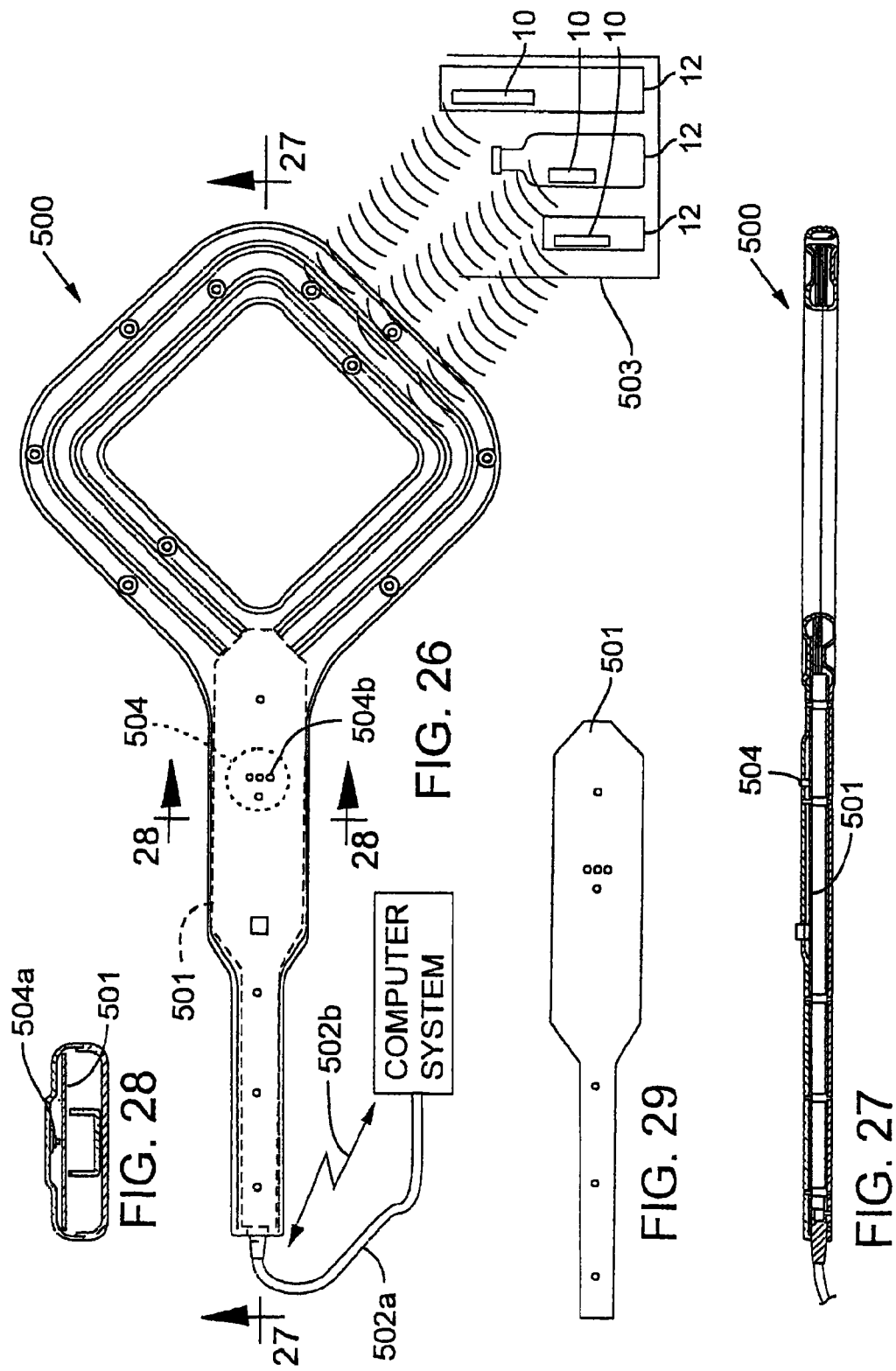

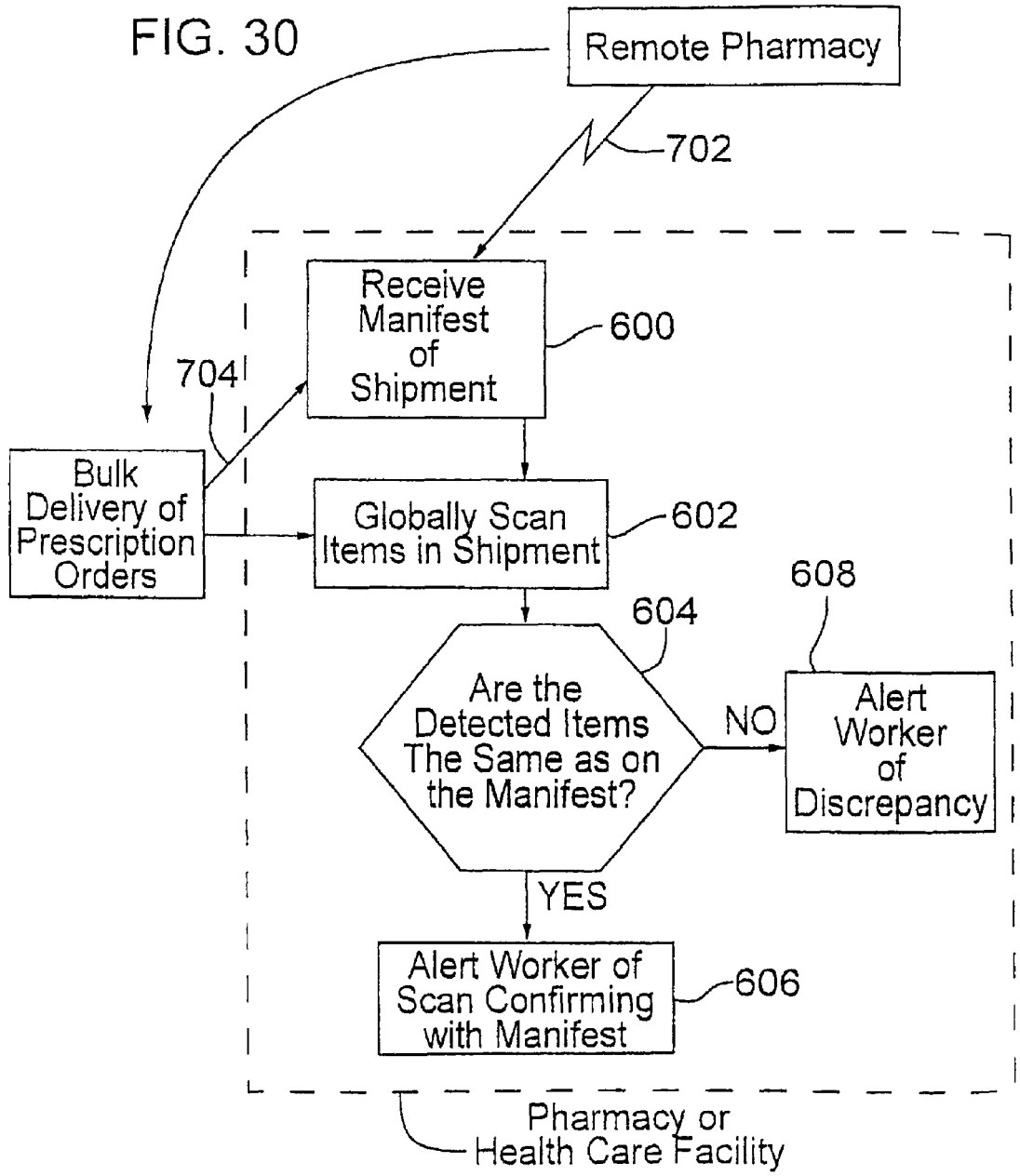

PHARMACY TRACKING SYSTEM WITH AUTOMATICALLY-ENTERED CUSTOMER TRANSACTION INFORMATION

This application is a continuation-in-part of U.S. patent application Ser. No. 13/050,308, filed Mar. 17, 2011, which claims the benefit of 61/444,062, filed Feb. 17, 2011 and is a continuation-in-part of U.S. patent application Ser. No. 12/268,389, filed Nov. 10, 2008, which is a continuation of U.S. patent application Ser. No. 11/213,321, filed Aug. 25, 2005, now U.S. Pat. No. 7,448,544, which claims priority to U.S. Provisional Patent Application No. 60/605,274, filed on Aug. 26, 2004, and which is a continuation-in-part of U.S. patent application Ser. No. 09/715,439, filed on Nov. 16, 2000, now U.S. Pat. No. 7,672,859. The entire disclosure of these references is hereby incorporated by reference.

In addition, U.S. patent application Ser. No. 13/050,308, filed Mar. 17, 2011 is a continuation-in-part U.S. patent application Ser. No. 13/027,075, filed Feb. 14, 2011, which is a continuation of U.S. patent application Ser. No. 10/223,308, filed Aug. 18, 2002, now U.S. Pat. No. 7,887,146, which claims priority to U.S. Provisional Application No. 60/313,305, filed Aug. 18, 2001. The entire disclosure of these references is hereby incorporated by reference.

FIELD

The present disclosure relates to a system for tracking a prescription order in a pharmacy and, more particularly, to a system for tracking, filling and storing a prescription as well as automatically entering customer transaction information upon dispensing of the filled prescription.

BACKGROUND

A typical local retail pharmacy fills thousands of prescription orders per week. Moreover, as the general population ages and new beneficial drugs are introduced, prescription order volumes to be filled at retail pharmacies are expected to rise sharply. This present and expected increase in order volume places enormous pressure on pharmacists and other pharmacy workers, who strive to fill each order efficiently, accurately and quickly.

Most customers have a limited view of how a typical retail pharmacy works. They often think that when they present a written prescription order to a local retail pharmacy, such as at their corner drugstore, a pharmacist will personally greet them, review their order, complete and file the necessary paperwork required by applicable laws, fill the prescription order, and present the filled order to the customer, all within a few minutes. However, in addition to increasing volume, the traditional retail pharmacist is now faced with a large variety of additional tasks, including obtaining proper insurance payment authorization, and in some cases verifying the reliability of a particular prescription order. Moreover, orders may now enter the pharmacy through a wide variety of mediums, such as via facsimile, phone call, and e-mail.

In light of the increasing demands and obligations placed on retail pharmacies, they are evolving into more efficient organizations having numerous employees performing individual tasks associated with filling each prescription order. For example, when a customer presents a prescription to the pharmacy, a clerk may take the prescription order and enter it into a computer system that verifies insurance information. If approved, he or she may then prepare a prescription label to be placed on the package that will ultimately contain the prescribed drug. The clerk may then present the prescription order and label to a technician, usually stationed at another location within the pharmacy, who will physically fill the prescription by placing the appropriate quantity of the prescribed drug within the bottle and attach the label. Pursuant to applicable laws, a registered pharmacist then reviews the technician's work, and approves the dispersal of the completed prescription order to the customer. A clerk may then place the filled prescription in a storage area to await customer pick-up. Upon customer pick-up, the clerk files the written prescription order and any other appropriate paperwork related to the transaction, such as signed insurance forms and any informed consent paperwork. This type of system allows the pharmacy to quickly, efficiently, and economically fill numerous prescription orders.

In addition, a growing number of retail pharmacies are using remote filling stations to process some prescription orders. In general, the retail pharmacy receives an order from a customer, and completes the necessary steps to fill the prescription. However, instead of filling the prescription order in-house, the request is transferred, usually electronically, to a remote filling station, that fills the order and ships the filled order back to the pharmacy for distribution to the client. Usually, all the orders processed from a particular remote filling station are shipped to the retail pharmacy in one container, and considerable paperwork usually accompanies the container to document the filling of each prescription order. Accordingly, considerable pharmacy worker time and effort is spent processing the bulk shipment of filled prescriptions and related paperwork, such as entering information into the retail pharmacy's computer system, and distributing the filled prescription orders to a storage area for individual customer pick-up.

Given the high volume of prescription orders being filled, the large number of people performing individual tasks associated with filling each prescription order, and the numerous locations within and outside of the pharmacy that a prescription order can be positioned as it is being filled, it is important that the prescription order, and ultimately the filled prescription, be easily located and identified throughout the process. For example, if a particular prescription order is denied payment by insurance, a clerk may hold the prescription order aside while the customer is contacted. If the customer presents himself to another clerk at the pick-up window, while the first clerk is attempting to call the customer at home, the second clerk often has no way of knowing the current status of the prescription order, or where it is in the order filling process. Accordingly, the second clerk is forced to search each location within the pharmacy.

In addition, should a prescription order be inadvertently misplaced within the pharmacy, it is often difficult to find, thereby needlessly delaying the filling process and wasting worker time to locate it. Similarly, it is desirable for pharmacy workers to be able to easily identify and locate particular prescription orders that meet predefined criteria, such as having fallen behind a promised customer pick-up time.

Some pharmacy vendors have attempted to overcome these problems by offering systems that manually track prescription orders within a pharmacy. In particular, they require the worker at a given station to manually enter into a computer the fact that they have received a particular prescription order at that particular location. However, in addition to the lost time associated with manually entering this information at each station, evidence suggests that many workers find this repetitive task cumbersome, and as a result, they often fail to manually enter such information. Accordingly, these types of tracking systems are rendered useless.

Similarly, some pharmacy vendors have attempted to automate the prescription filling aspect of a pharmacy by incorporating an automatic assembly line process for filling prescription orders. In particular, an operator enters a prescription order into a computer system, which causes a conveyor-type system to deliver an empty vial to an automated drug dispenser. The filled vial is then automatically matched with a label and presented to a pharmacist for final review and approval. While these types of devices facilitate the quick and efficient filling of prescription orders, they are expensive for use in a retail pharmacy environment, and they occupy a large amount of limited space within the pharmacy. Moreover, they still require pharmacy workers to perform manual tasks such as verifying insurance and renewability of the prescription, and processing the various forms of prescription orders before and after they are entered into the automated system. Accordingly, they do not permit the easy location of prescription orders as they travel within the automated pharmacy environment, or easy identification of the prescription orders that have fallen behind a predetermined timeframe established for the pharmacy to fill the prescription order.

Moreover, once the prescription order has been filled, the prescriptions are often organized and stored in one or more collection bins for pick-up. Oftentimes, the prescriptions are organized in alphabetical order according to the patient's last name. This can lead to confusion and/or risk of dispensing the prescription to the wrong patient. For instance, if there are two patients with substantially similar names, the prescriptions are likely to be stored next to each other, and the pharmacy worker may inadvertently dispense a prescription to the wrong person without adequately confirming the customer's identity.

SUMMARY

Despite the known pharmacy prescription order identification and tracking systems, there remains a need for a method of conducting a transaction involving transfer of a filled prescription order from a pharmacy to a customer. The method includes detecting that a filled prescription order is available for transfer from the pharmacy to the customer. Upon detecting that the filled prescription order is available for transfer from the pharmacy to the customer, the method includes: 1) automatically notifying the customer that the filled prescription order is available for transfer from the pharmacy to the customer; 2) automatically populating a form with at least one piece of customer information, wherein the form is intended for signature by the customer to signify transfer of the filled prescription order from the pharmacy to the customer; 3) automatically providing a sale price for the filled prescription order; 4) automatically providing medical information about the filled prescription order; and/or 5) automatically updating an inventory of filled prescription orders stored within the pharmacy.

A method of conducting a transaction involving transfer of a filled prescription order from a pharmacy to a customer is also disclosed. The method includes depositing a filled prescription order into a storage area for storage and detecting removal of the filled prescription order from the storage area. Additionally, upon detecting removal of the filled prescription order from the storage area, the method includes automatically obtaining transaction information to facilitate transaction of the filled prescription order from the pharmacy to the customer.

Still further, a method of conducting a transaction involving transfer of a filled prescription order from a pharmacy to a customer is disclosed. The method includes receiving a prescription order that becomes the filled prescription order and moving the prescription order along a workflow stream by moving the prescription order by hand between a plurality of physically spaced apart locations to manually fill the prescription order. Moreover, the method includes automatically tracking the prescription order within the pharmacy as the prescription order moves along the workflow stream to become the filled prescription order. Additionally, the method includes detecting that the filled prescription order is available for transfer from the pharmacy to the customer. Upon detection that the filled prescription order is available for transfer from the pharmacy to the customer, the method includes automatically notifying the customer that the filled prescription order is available for transfer from the pharmacy to the customer. Furthermore, the method includes depositing the filled prescription order into storage and receiving a pick-up request for the filled prescription order from the customer. The method further includes detecting removal of the filled prescription order from storage and upon detecting removal of the filled prescription order from storage, the method includes performing: 1) automatically obtaining and populating a form with at least one piece of customer information, the form intended for signature by the customer to signify transfer of the filled prescription order from the pharmacy to the customer; 2) automatically providing a sale price for the filled prescription order; 3) automatically providing medical information about the filled prescription order; and 4) automatically updating an inventory of filled prescription orders stored within the pharmacy.

Additional objects and advantages of the present disclosure will be apparent from the detailed description of the preferred embodiment thereof, which proceeds with reference to the accompanying drawings.

BRIEF DESCRIPTION OF THE DRAWINGS

FIG. 1 is a schematic diagram of an identification tag in accordance with an embodiment of the present disclosure.

FIG. 2 is a schematic diagram of an exemplar retail pharmacy using a remote filling station to fill one or more prescription orders, and return the filled prescriptions to the retail pharmacy for distribution.

FIG. 3 is an isometric view of simultaneous scanning of a plurality of prescription orders in accordance with an embodiment of the present disclosure.

FIG. 4 is an isometric view of a prescription order having a tag operably secured thereto with the tag having a plurality of transducers thereon.

FIG. 5 is a schematic view of a prescription order tracking system used in a remote pharmacy in accordance with a preferred embodiment of the present disclosure.

FIG. 10 is a top plan view of an exemplar, planar, antenna array card showing possible shielding encircling each antenna.

FIG. 11 is a top, side, and back view of the antenna array card of FIG. 10.

FIG. 12 is a front isometric, exploded view of a storage bin having an antenna array card operably secured thereto.

FIG. 13 is a rear, isometric, exploded view of the storage bin and antenna array card of FIG. 12.

FIG. 15 is a front, isometric view of the storage structure of FIG. 14 showing a possible connection to a computing device.

FIG. 16 is a side view of the storage structure of FIG. 15.

FIG. 17b is an alternative exemplar, isometric view of a possible workstation having a substantially horizontally mounted planar frame containing at least one tag reader antenna therein.

FIG. 18 is a top view of the workstation of FIG. 17a.

FIG. 19a is a top view of an exemplar array of tag reading antenna directed to define a common scanning space or scanning tunnel.

FIG. 19b is a top view of an alternative exemplar array of tag reading antenna.

FIG. 26 is a schematic view of a scanning wand in accordance with an embodiment of the present disclosure.

FIG. 27 is a right, side view of the scanning wand of FIG. 26.

FIG. 28 is a cross-sectional view of the scanning wand of FIG. 26 taken along line 28-28 of FIG. 26.

FIG. 29 is a top view of a preferred conductive portion of the scanning wand of FIG. 26.

FIG. 30 is exemplar control logic for using the scanning wand of FIG. 26 with the tracking system of the present disclosure.

DETAILED DESCRIPTION OF PREFERRED EMBODIMENTS

A prescription order tracking and distribution system is disclosed in FIGS. 1-31. In general and as shown in FIGS. 5, 6A, 6B, and 20, a prescription order 12 is presented to the pharmacy 14 by a customer or patient. The order 12 can be received by a pharmacy worker, a healthcare provider or other agent (hereafter collectively referred to as a "healthcare provider") of a patient. Once the prescription order 12 is received, the order 12 is processed and filled within the pharmacy 14 such that the "prescription order" becomes a "filled prescription order." Also, the filled prescription order can be stored (e.g., at a will-call storage area) until the customer comes back to the pharmacy 14 to pick up the filled prescription order.

Figure 6A:
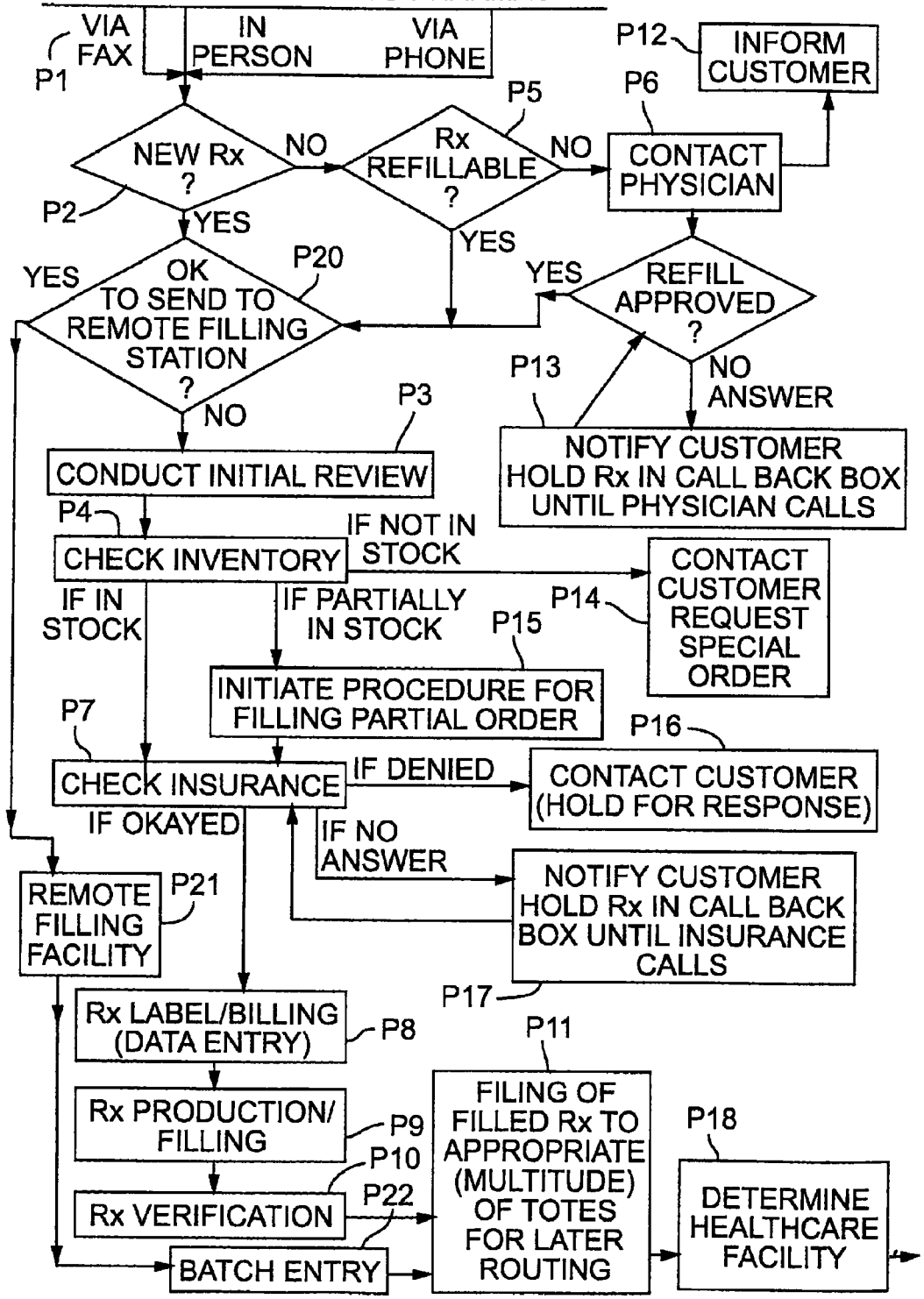
FIG. 6A is a block diagram of an exemplar health care provider prescription order filling system showing a possible remote pharmacy filling process.

Referring to FIGS. 4 and 6A, the pharmacy or the healthcare provider assigns an identification tag 16 to the prescription order 12. Tag reading devices 18 are positioned at key locations throughout the pharmacy 14 (FIG. 5) and the healthcare provider's facility 17 (FIG. 21) and in communication with a computer system 20 having a display 22, such that the movement of the prescription order 12 throughout the pharmacy 14 and/or the healthcare provider's facility 17 automatically detects and records the location of the tag 16 without further worker input. A plurality of tags may be simultaneously tracked, thereby facilitating bulk processing and distribution of prescription orders, particularly those received from the off-site facility 15. Moreover, each tag preferably includes read-writable memory that is preferably coded with key information about the prescription order, such as the customer's name, identifying information, prescribed drug, insurance information, directions for use, National Drug Control ("NDC") number, and the like. Accordingly, a pharmacy worker within the pharmacy, a worker at the healthcare provider's facility or even a worker at a third remote location can quickly and easily determine all relevant information about a particular prescription order without necessarily having to first correlate a tag identification code with a computer system database.

In addition, a worker can easily determine the location of the prescription order 12 within the pharmacy and/or the healthcare provider's facility 17 by entering commands in the computer system 20 with a user input device such as a keyboard 120 to display the location of the prescription order 12 on the computer display 22. The individual elements forming the present disclosure are discussed in greater detail below.

A. Tags

Preferably, one or more readers 18 locate tags 16 through electromagnetic interrogation of a spatial region to determine the presence of an object. One such system is disclosed in U.S. Pat. No. 6,057,756 to Engellenner, the disclosure of which is hereby incorporated by reference. In general, the tag 16 is an electromagnetic antenna and/or signal receiver which responds either passively or actively to announce the presence (or absence) of an object within a controlled region defined by a broadcasted electromagnetic interrogation signal. Preferably, each tag 16 includes a coding mechanism for uniquely identifying it with respect to other tags in the system.

FIG. 1 discloses an exemplar tag 16 and related components for locating a prescription order 12 in a pharmacy 14.

The computer system 20 is operably connected to a transceiver 60a, such as for example, a conventional Radio-Frequency Identification ("RFID") tag, that transmits a signal 42 to a plurality of tags 16. Each tag 16 is assigned to travel with a unique prescription order 12, and includes a transceiver 60b for receiving the signal and internal circuitry such as a processor 48, power source 50 and memory 52 which contains a unique identifier for that tag and control logic to preferably activate one or more transducers 17, which serve as the worker signaling device when the tag 16 receives a unique signal 42 from the transmitter 40. Such transducers 17 may also be operably secured to the tag reader 18 or some other structure as needed to assist a worker.

Preferably, the transducer 17 is either a light 17a (FIG. 4) or audio speaker 17b (FIG. 4). More preferably, there are a plurality of transducers 17 that can be individually activated on each tag 16. For example, there can be three lights of different colors (i.e. red, yellow, and green), which can be activated either alone or in combination to identify the status of that prescription order 12, with a different status being denoted by a different transducer being activated.

More preferably, the memory 52 on the tag is read-writable and is preferably coded with key information about the prescription order, such as the customer's name, identifying information, date of birth, social security number, prescription number, proper storage instructions, known side-effects, expiration date, prescribed drug, insurance information, directions for use, National Drug Control ("NDC") number, and the like.

The computer system 20 includes appropriate application programs 136 (FIG. 7) and memory 122 (FIG. 7) to correlate a customer's identifying information such as their name, phone number, and the like, with the unique identifier and/or other information in the memory of the tag traveling with that prescription order. Accordingly, when a pharmacy worker wishes to locate a customer's prescription order, he or she may find the customer's identifying information on the computer system 20, and cause the computer system to transmit the unique signal 42 through the transceiver 60a to wirelessly activate one or more transducers 17 on the tag 16 associated with the customer's prescription order 12. For example, the tag's audio speaker 17b may make an audible sound, or one or more lights 17a on the tag 16 may light and/or blink.

Preferably, a plurality of fixed or handheld transceivers, which are collectively referred to as tag readers 18 herein, are spaced apart from each other and positioned at desired locations within the pharmacy 14 to define spaced-apart interrogation zones within the pharmacy. Each tag reader 18 includes a front-end transmitter 62 that generates a digitally encoded signal 64. Preferably, the signal 64 is chosen to facilitate a response from only one uniquely coded tag 16. The receiver portion 66 of the tag reader 18 can induce a coded signal detector that senses the transponder signal 64 and correlates it with a stored code to identify that the tag 16 is present in a particular interrogation zone, thereby also determining the tag's location within the pharmacy.

The computer system 20 can also use conventional triangulation techniques to determine the location of the tag within the pharmacy. In which case, only two spaced-apart tag readers 18 need be placed within the pharmacy. Alternatively, using quasi-sonar-type locating techniques, a single tag reader 18 could be used determine the location of the tag within the pharmacy.

Each tag 16 can be either passive or active. In the passive mode, the tag circuitry accumulates and then returns a signal, if the interrogation signal matches a predefined code sequence stored in memory in the tag's circuitry. In an active mode, each tag further includes a power source 50 that assists with signal amplification, detection and/or wave forming.

Figure 25:
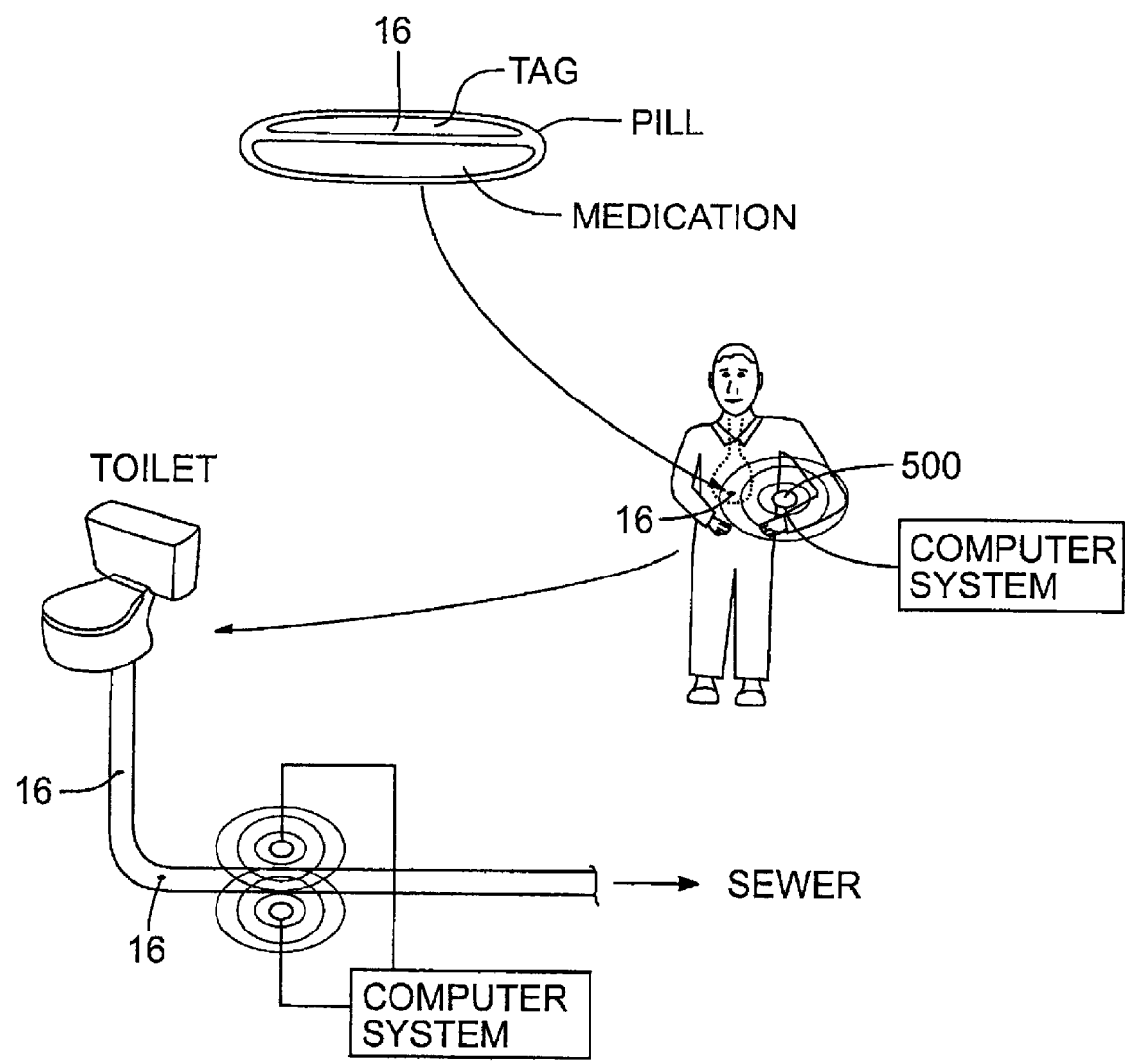
FIG. 25 is a schematic diagram of an exemplar biologically activated tag operably secured to a medication.

More preferably and as shown in FIG. 25, miniature tags are also operably secured to individual doses of medication. Preferably, such miniature tags are no larger than a grain of rice, and they are operably secured to the medication, say for example by being received within the casing of a pill or the like. Accordingly, tag readers, which are in communication with a computer system, are positioned near the patient's stomach or near the waste of the patient, to detect the presence of a tag thereby indicating the medication has been consumed by the patient.

In institutional environments where a large number of residents consume medications on a regular basis, a tag reader can be positioned along a common waste removal path, such as a sewage pipe or the like exiting from the facility. Accordingly, the tag reader can detect each tag as it exits the facility along the waste path, thereby providing non-evasive verification of consumption medication for all patients within the facility.

Preferably, unique tags are also operably secured to each worker and the patient themselves. Accordingly, the computer system correlates the prescription orders, patients, and worker information to determine if a particular patient has been given their prescription order, if the correct prescription order was distributed, which worker administered it, and if the medication was indeed consumed by the patient.

More preferably, tags operably secured to the medications are biologically activated, say for example, by interacting with stomach acids or digestive processes to activate them to thereby further serve to confirm proper ingestion of the medication. One such biologically activated structure includes impeding an activation switch of the tag within an ingestible material, such as calcium carbonate or the like, that dissolves in stomach acid. The switch is biased to an on position, but imbedded in the ingestible material in an off position. As the ingestible material dissolves, the switch is released and thereby seeks its on position to activate the tag.

Other examples of biologically activated structures include encasing the tag within an ingestible electromagnetic shielding material, such as a human safe metal or the like. The shielding material prevents the tag from communication with a tag reader. However, as the shielding material dissolved in a patient's stomach acid, the tag and tag reader are able to communicate. Also, a biologically activated structure can also be a tag having a current passing through a small amount of ingestible, conductive material that dissolves in stomach acid thereby defining a resistor. As the ingestible, conductive material dissolves, the resistance provided by the resistor is reduced. The tag detects this change in resistance and activates itself to communicate with a tag reader accordingly.

Individually tagged pills and the like provide several additional benefits. For example, they reduce the likelihood of counterfeit medications being dispensed, they can include monitoring sensors that track environmental conditions such as temperature, humidity, light levels and the like, to alert a worker or potential user that a particular dose had been stored in improper conditions and the effectiveness of the dose may therefore have been compromised, and they help stop "shrink" or other diversion of the medication.

In addition, they facilitate accurate counting of medications and assist with preventing inadvertent dispensing of medications. For example, pills can become lodged within the shots of traditional automated pill counters. Such pills can become dislodged during the filling of a new prescription and inadvertently fall into a bottle for a different patient. Individual pill tracking can detect such errors and validate quantity simply by scanning a filled prescription bottle at any time prior to dispensing it to a customer.

B. Prescription Order Tracking

Tags 16 may also be used to track the location of the prescription order as it travels throughout the off-site pharmacy 14 an off-site prescription filling center 15 and/or a healthcare facility 17. For example and referring to FIG. 5, a prescription order 12 is presented to the pharmacy 14 and assigned an identification tag 16, preferably with one or more transducers 17 thereon. Tag readers 18 are positioned at key locations throughout the pharmacy 14 and in communication with the computer system 20 having a display 22, such that the movement of the prescription order 12 throughout the pharmacy 14 automatically detects and records the location of the tag 16 without further worker input. In addition to, or alternatively, the transducers 17 can be operably secured to a tag reader 18 or some other object.

Accordingly, a worker can easily determine the location of the prescription order 12 within the pharmacy by entering commands in the computer system 20 with a user input device such as a keyboard 120 to display the location of the prescription order 12 on the computer display 22. Alternatively, the computer system can detect the identity of a customer based on predetermined criteria such as by detecting a tag operably secured to the customer, or through bio-medical detection techniques such a retina or fingerprint scanning, and initiating retrieval of the detected customer's prescription order.

Each tag reader 18 is placed in communication with the computer system such that information regarding the customer, his prescription order position, and the status of his order can be readily displayed on the computer display 22, and thereby facilitating location of the prescription order 10 within the pharmacy 14.

Preferably, the identification tags 16 are attached to the prescription label, detachably secured to the prescription order, or rigidly secured to a carrier 46 (FIG. 4) containing these documents and other materials related to filling the prescription. The tags themselves can be either rigidly or detachably secured to the prescription order. For example, the tags can be directly secured to the prescription with adhesive or secured within a prescription lid. Also, the tags can be secured to a fastener, such as a paperclip, that is detachably secured to the prescription order.

1. Pharmacy Prescription Order Filling Procedure

Referring specifically to FIG. 6A, an exemplary pharmacy, which is preferably a remote pharmacy for filling prescription orders for a healthcare facility 17 (FIG. 17) prescription order filling procedure is disclosed. In step P1, the healthcare facility presents a prescription order, which could include a written prescription form, a renewable prescription label, or any other tangible medium documenting a request for a prescription by a health care provider is presented to the pharmacy either in person, via facsimile, via phone, or via a computer transmission, such as e-mail. A pharmacy worker then reviews the prescription order and attaches a unique tag 16 (FIG. 4) to it that is readable by a tag reader 18 (FIG. 4) to determine its location within the pharmacy 14.

As shown in Step P2, the pharmacy worker then determines if the prescription order is for a new prescription. If not, the worker determines if the prescription is refillable (Step P5). If the prescription is not refillable, the pharmacy worker will typically contact the physician or the physician's office to determine if the prescription should be refilled (Step P6). If the physician denies a refill, the customer is informed (Step P12). If the physician does not answer the customer is notified and the pharmacy typically holds the prescription order until the physician calls back (Step P 13).

If the pharmacy worker ultimately determines that the prescription order is fillable, by the answers to any of Steps P2, P5, or P6 being affirmative, the pharmacy worker then must typically determines if the prescription order is able to be sent to a remote filling facility or if it will be filled onsite within the pharmacy itself (Step P20).

a. Onsite Filling of Prescription Order

If the pharmacy worker determines that the prescription order is to be filled onsite, he or she first conducts an initial review (Step P3) which includes checking the available inventory for the prescribed drug (Step P4), determining if there is available insurance (Step P7) and if required, obtaining approval from the insurer and preparing the label and necessary billing and information disclosure paperwork (Step P8).

Regarding Step P4, if the inventory is not in stock, the pharmacy worker typically informs the customer and offers the customer an opportunity to special order the prescribed drug (Step P14). If there is only a partial amount of the prescribed drug in stock, the pharmacy worker will typically initiate a procedure for filling only a partial order (Step P15). This procedure typically includes preparing additional paperwork to alert the customer that only a partial order has been filled, and ordering additional quantities of the prescribed drug.

Regarding Step P7, if the insurance coverage is denied, the prescription order is typically held in an area pending the customer being contacted to request authorization to proceed (Step P16). If the insurer cannot be contacted, the pharmacy has the option to either fill the prescription and alert the customer upon pick-up, or hold the prescription order pending a response from the insurer (Step P17).

After the initial review is complete, the prescription order and related paperwork is presented to a technician for data entry (Step P8) and filling (Step P9), the technician fills the prescription order and attaches the label. The technician then presents the filled prescription order and related paperwork to a registered pharmacist for verification (Step P10).

Following verification, the filled prescription is placed in a storage area pending delivery to the healthcare provider (Step P11). Preferably, the healthcare provider has many patients needing prescription orders therein, and the remote pharmacy fills a plurality of prescription orders, usually for different patients, for the healthcare facility. In such case, these orders for a common healthcare provider are preferably individually identified, but grouped together in a common tote or the like, so that they may all be transported to the healthcare provider in the same shipment or delivery run.

Preferably, the totes are delivered to the healthcare provider by a courier, such as a driver or the like as shown in step P23. In such case, the driver receives the totes and a related manifest of the prescription orders and their related patient identifying information therein. This manifest is preferably in a computer readable medium. The driver usually verifies the totes and signs that he or she has received them. The driver then organizes the totes for delivery (Step P24). More preferably, the totes and the delivery vehicles include tags and/or tag readers in communication with the computer system to allow tracking of prescription orders through this phase of the distribution process.

Upon delivery of the tote to the healthcare facility, a healthcare worker usually inspects the prescription orders and related manifest to determine if these materials are in order (Step P25). If so, the healthcare worker signs that he or she has received them, and then transfers the individual prescription orders to a holding area for distribution to individual patients within the healthcare facility (Step P26).

If not, the healthcare worker has a number of options including preparing an exceptions list (step P27), notifying the remote pharmacy of the discrepancy (step P28), and/or determining the criticality of the discrepancy (step P29). If the discrepancy is critical, the pharmacy can refill the missing or erroneous prescription order (step P8). If the discrepancy is not critical, steps P30 through P36 or the like can be taken.

b. Filling at Remote Filling Facility

If in Step P20, the pharmacy worker determines that the prescription order should be filled at an off site remote filling facility, the prescription order is transmitted to an off-site facility, usually electronically as shown in FIG. 2. In such case, the remote filling facility will attach a new tag to the prescription order, and if equipped with one, may code the tag's read-writable memory 52 (FIG. 1) with appropriate drug identifying and other information about the prescription order.

At the remote filing facility, the prescription order is filled in compliance with traditional filling practices, procedures and regulations, including conducting an initial review, checking insurance, labeling, data entry, filling, and verification (Step P21). The filled prescription order is then combined with other filled prescription orders to be delivered to the pharmacy and transported essentially in bulk to the pharmacy as shown in FIG. 2. Alternatively, the filled prescription orders may be delivered directly to the healthcare provider's facility (step P11) preferably though a delivery system substantially similar to those previously described in steps P23-P36.

Upon arrival at the pharmacy or healthcare provider's facility, the bulk shipment of filled prescription orders are preferably positioned in bulk within an interrogation zone of the computer system (Step 22), which simultaneously reads the tag 16 on each prescription order in the bulk shipment as shown in FIG. 3, and updates the computer system's records with this information, including any new information added by the remote filling facility to the tag's memory 52 (FIG. 1).

More preferably, and referring to FIG. 26, the interrogation zone includes a scanning wand 500 in communication with the computer system. This communication can be provided by a wired link between the wand and the computer system or the wand can be wireless connected to the computer system using known technology such as wireless fidelity (WiFi) or Bluetooth technology or the like. In one preferred embodiment, the wand is hand-held.

Preferably, in cases where the tags are radio frequency identification tags, the scanning wand 500 can be an antenna from a Radio Frequency Identification Tag reader. Preferably, the loop is diamond shape and positioned at the distal end of the wand. Alternatively, the tag reader can be operably secured within the wand itself, say for example, by securing it within the handle portion of the wand.

More preferably and referring to FIGS. 26-29, the wand 500 includes a circuit board 501 with related circuitry thereon and a power source to activate one or more transducers 504 thereon in response to predetermined criteria. For example, the transducers can includes a speaker 504a and/or lights 504b that are activated by the computer system in response to the detected presence or lack thereof of one or more prescription orders from the bulk shipment. Alternatively, the transducers can be spaced apart from the wand, such as being positioned on a separate consol, pad, mini-console, or the like. The feedback provided by the transducers allows a worker to be away from a computer terminal or the like and still obtain meaningful information about the scanned shipment.

If desired, the wand can be slid into a holster or cradle (not shown) adjacent to the interrogation zone. Accordingly, it need not be held over the items to be scanned. Rather, the items to be scanned can simply be placed near the wand. If desired, a plurality of wands can be positioned along an area so as to define a tunnel through which all prescription orders entering the pharmacy or healthcare facility must pass upon arrival. This plurality of wands can be multiplexed together as described elsewhere herein.

As shown schematically in FIG. 30, the scanning wand 500 and related computer system can be used to verify that a bulk shipment 503 (FIG. 26) of prescription orders arriving at a pharmacy or healthcare facility conforms to a manifest of that shipment. First, a manifest is provided to the pharmacy or health care facility (Step 600). This manifest can arrive through a variety of ways. For example, it can be transmitted from the remote pharmacy 702, be provided on a computer readable media along with the shipment 704, or it can be obtained from one or more read/write identification tags contained within the shipment.

A worker then places the entire shipment in the interrogation zone of the scanning wand. (Step 602), wherein the identification tags of each prescription order is detected and read by the computer system. The computer system then compares the detected prescription orders with the manifest and determines if all items on the manifest are present in scanned order (Step 604).

If all the items in the manifest are present, the computer system and/or wand alert the worker that the scan conformed to the manifest (Step 606). This can be accomplished by activating one or more transducers, such as by giving an affirming chime or the like. If one or more items in the manifest are missing from the scanned items, the computer system and/or wand alert the worker of this discrepancy (Step 608). This can be accomplished by activating one or more different transducers, such as by initiating a warning siren and/or lighting a red light. Accordingly, a worker can instantly know if a particular shipment is complete simply by performing one global scan of the shipment.

Preferably, the computer system also tracks and records each detected individual prescription order as having arrived at the pharmacy and/or healthcare facility.

2. Pharmacy Tracking Zones

In practice and referring specifically to FIG. 5, it is more efficient to perform the various steps noted above at spaced apart locations, or zones, throughout the pharmacy. For example, prescription order intake (Step P1 of FIG. 6) and initial review (Step P3 of FIG. 6) can be performed at location 21 (FIG. 5). Label printing and data entry (Step P8 of FIG. 5) could be accomplished at location 27 (FIG. 5). Prescription orders waiting from some form of call back either from the customer, the insurer, or the health care provider could be placed at location 27 (FIG. 5). Orders waiting to be filled could be placed at location 28 (FIG. 4), orders waiting pharmacist review and approval could be place at location 23 (FIG. 4), and approved filled prescription orders could be stored at location 30 (FIG. 4). Obviously, additional zones (24

& 25) could be added to accommodate a particular pharmacy's practices and procedures.

Preferably each station includes a tag reader 18 in communication with the computer system 20 for automatically detecting the arrival of the tag 16 attached to the prescription order 12 as it enters each location. More preferably, the tag reader 18 detects both the arrival of the tag 16 in that station, and the departure of that tag 16 from that station, with the time interval at that station being determined and recorded therefrom.

Each tag reader 18 is preferably fixed at a particular location so that detecting the presence of a tag near the device also automatically indicates the location of that tag 16 within the pharmacy. The tag readers 18 can be rigidly mounted to a work area or station, or portable (i.e. handheld) devices that are operably connected to the station so that it can indicate a location within the pharmacy of a detected tag. Such portable devices facilitate scanning of prescription orders that are compiled in bulk, such as a container of filled prescriptions arriving from an off-site filing facility (Step P22, FIG. 6). Since each prescription order in the container has a unique tag 16 the tag reader 18 can simultaneously detect and record the location of multiple prescription orders, a pharmacy worker can wave the tag reader 18 over the container to record the location of all prescription orders in the container and obtain information recorded in the read-writable memory of each tag.

Similarly, a healthcare worker at a healthcare facility can use the same or a similar system within the healthcare facility to wave a tag reader over a container to record the location of all prescription orders in the container and obtain information recorded in the read-writable memory of each tag.

3. Storage Bin

Space and efficiency can be optimized by storing filled or prescription orders 12 to be held for bulk distribution to the healthcare facility 17 a common storage bin 30, preferably containing a plurality of individually identified cubbies therein.

4. Portable Prescription Order Distribution Cart and Storage Bin

Figure 6A:
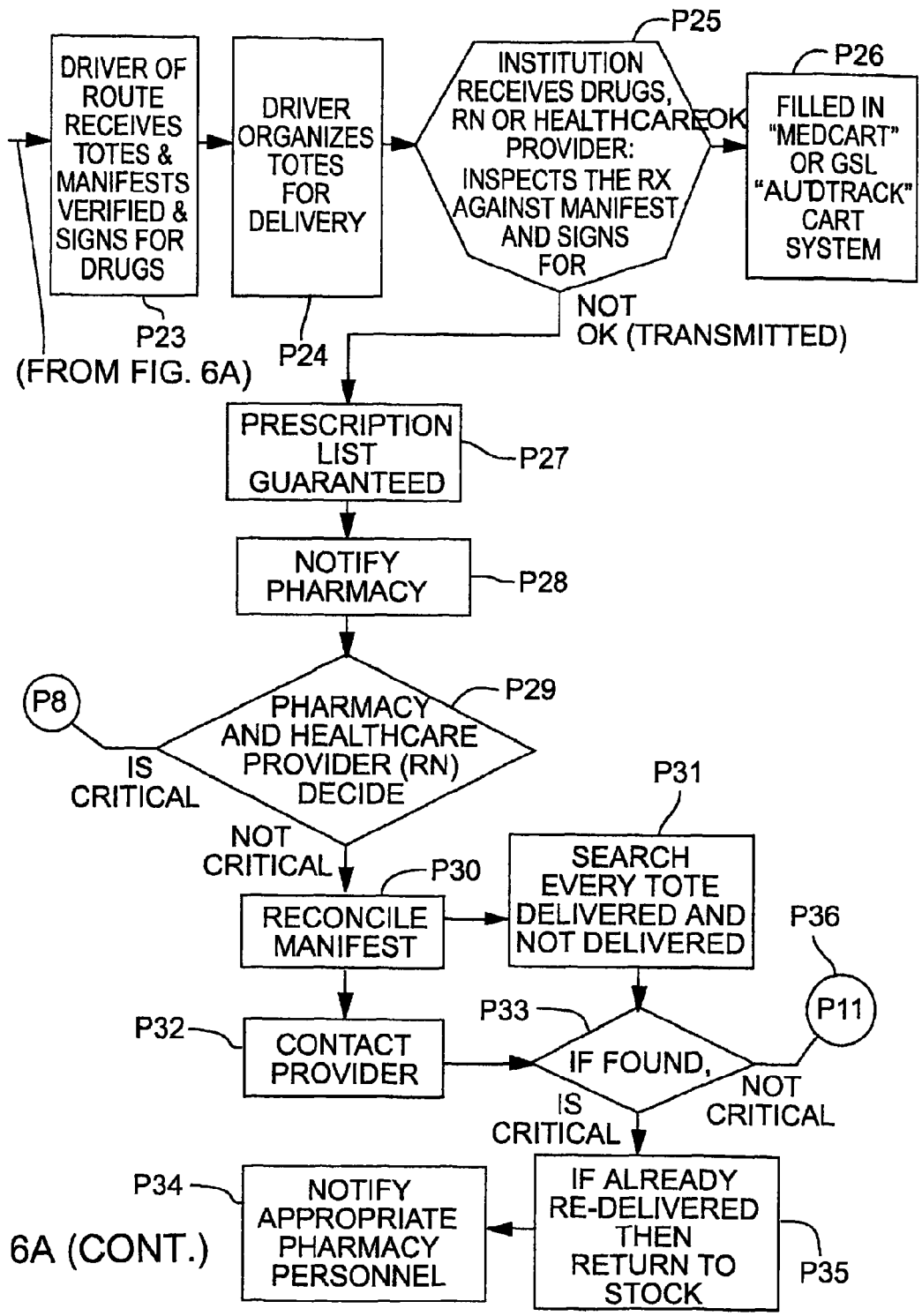
Figure 6B:
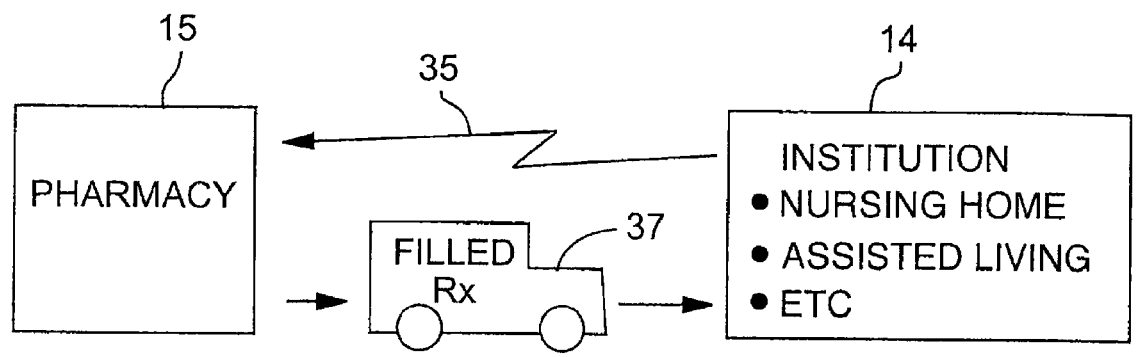
FIG. 6B is a schematic diagram of an exemplar health care provider prescription order filling system showing a possible distribution of a prescription order from the remote pharmacy of FIG. 6A to the health care provider for further distribution to a patient or resident.

Preferably, and as best shown in FIGS. 6A & 6B, the filled prescription orders for a particular healthcare facility are preferably distributed in bulk to the healthcare facility where they are separated and individually administered to the correct patients. Preferably, the healthcare facility includes tag readers in communication with either their own computer system or the same computer system of the pharmacy to allow the information associated with the tags to be transmitted to the healthcare facility along with the filled prescription orders. Alternatively, if the tags include read-writeable memory, the memory of each tag includes appropriate identifying information to correlate each filled prescription order with a particular patient.

Preferably, the healthcare facility has either a storage bin or a portable storage cart for easy storage, location, and removal of each patient's filled prescription order upon receipt from the remote pharmacy. Both of these storage devices are discussed in greater detail below.

a. Storage Bin

Figure 14:
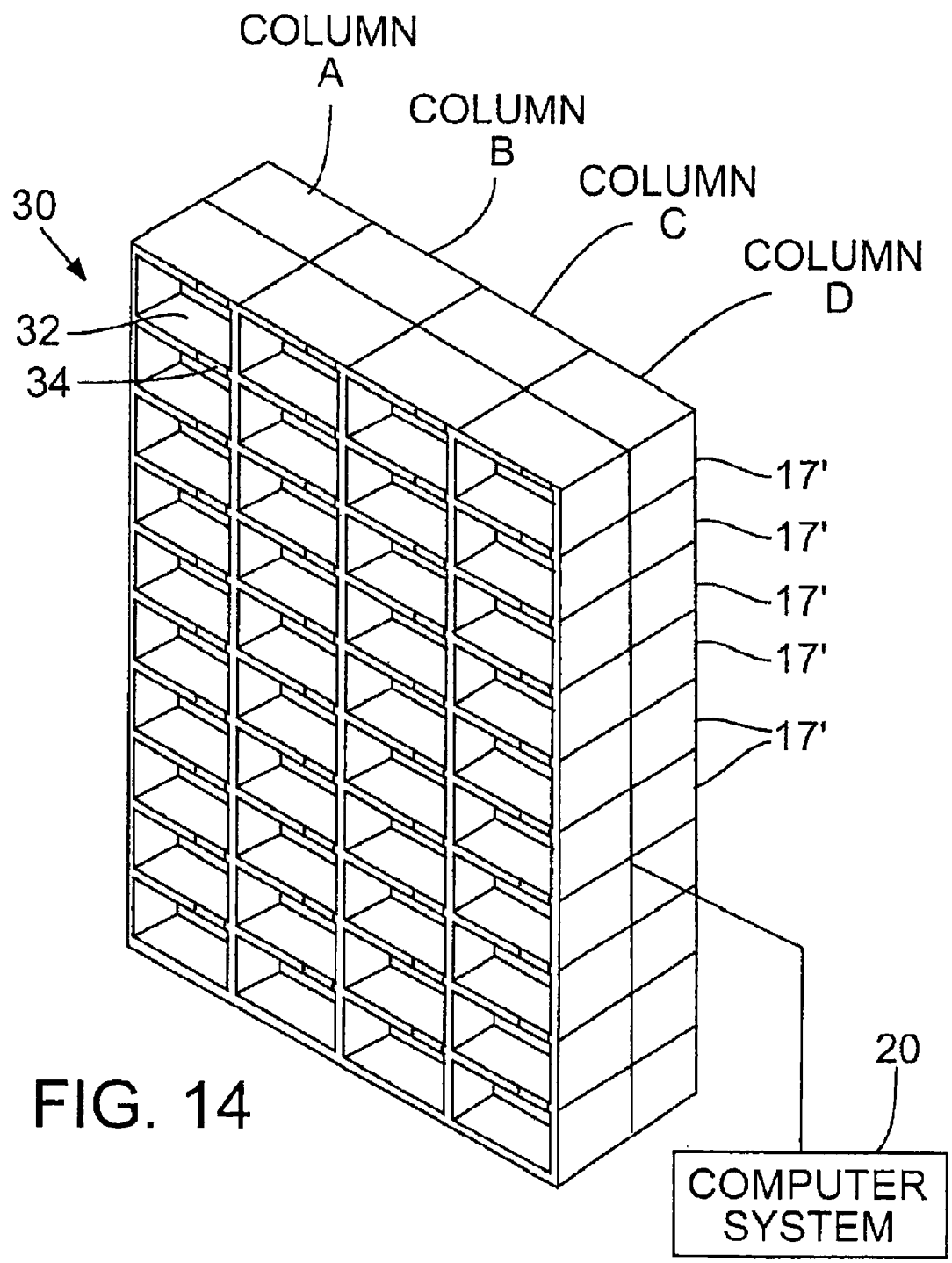
FIG. 14 is a front, isometric view of a storage structure having a plurality of antenna array cards operably secured thereto.

As best shown in FIGS. 14-16, the storage bin 30 preferably includes a plurality of cubbies 32, with each cubby 32 being sized to receive a prescription order 12 and associated filled prescription therein. Each cubby is uniquely identified 34, such as by being individually numbered, and includes a tag reader 18, which is preferably an economical antenna or the like operably secured to a common tag reading device by a switching device 36 (which is also commonly known as a multiplexer) for determining whether a particular tag 16 is received within it. Each tag reader 18 is preferably periodically in communication with the computer system 20.

When a prescription order 12 is filled, the prescription order 12 and filled prescription are simply inserted into an available cubby 32. Accordingly, the tag reader 18 associated with that cubby 32 sends a signal to the computer system 20 denoting the particular location and cubby number where the prescription order 12 and filled prescription are held. When a customer arrives to pick-up his or her filled prescription or when a healthcare provider worker seeks to distribute a particular filled prescription order to a patient, the worker enters the customer's identifying information into the computer system 20, and the particular bin number of the cubby containing the prescription order 12 and filled prescription or the current location in the filling process is displayed. The worker then locates and removes the filled prescription from the identified cubby and presents it to the customer or administers it to a patient as needed.

Alternatively, and/or in addition to determining the cubby number in which the customer's filled prescription order is located, the computer system can activate one or more transducers 17 positioned near the filled prescription order or on the tag 16 secured to the prescription order to alert the worker of its location.

The removal of the prescription order 12 from that particular cubby 32 is detected by the tag reader 18 and reported to the computer system 20. The tag 16 can remain affixed to the prescription order 12 when filed, thereby allowing it to be easily located in the future. Alternatively, the tag 16 may be reused with a new incoming prescription order.

b. Portable Prescription Order Distribution Cart

Figure 20:
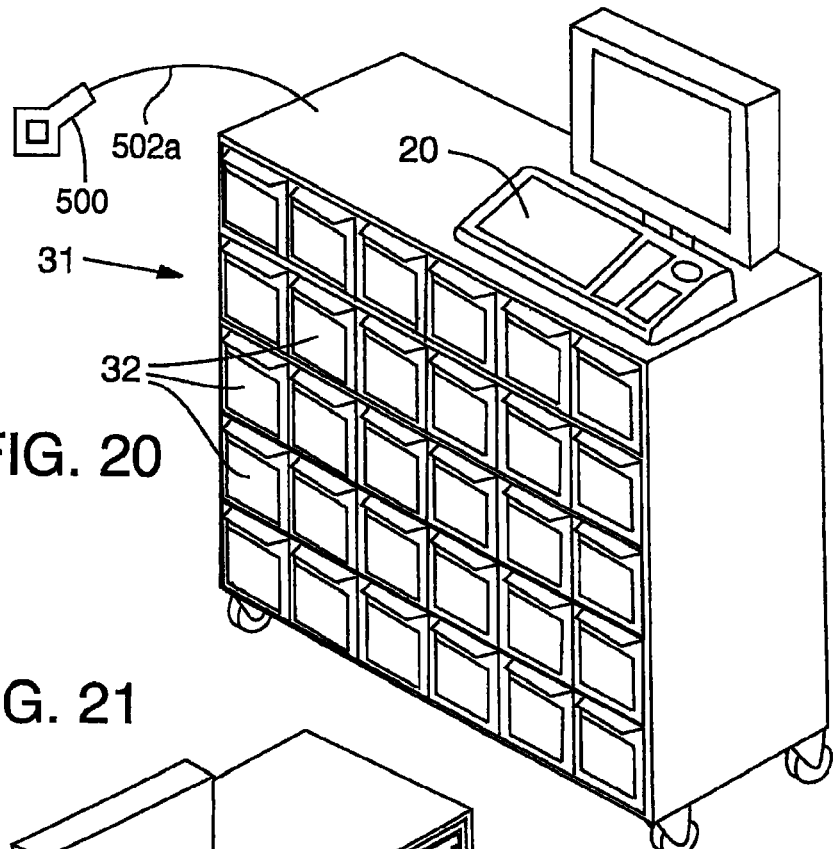
FIG. 20 is a front, isometric view of a portable prescription order distribution cart in accordance with an embodiment of the present disclosure.
Figure 21:
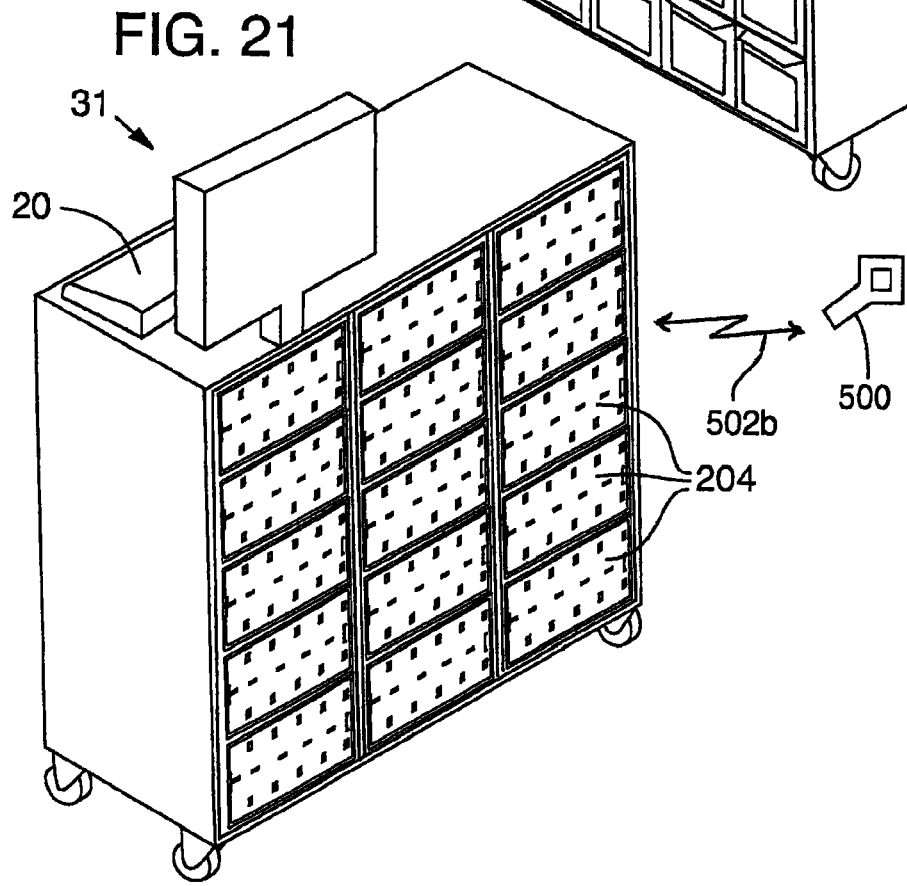
FIG. 21 is a rear, isometric view of the portable prescription order distribution cart in accordance with an embodiment of the present disclosure.
Figure 22:
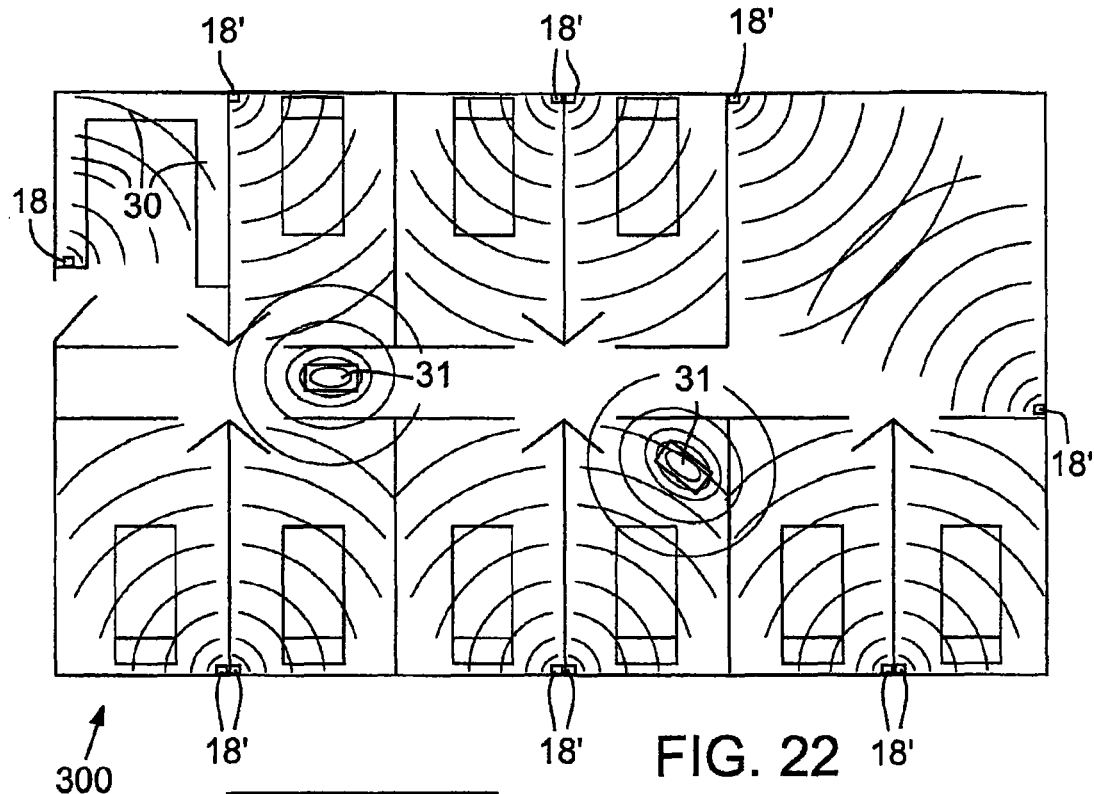
FIG. 22 is a schematic view of a health care provider prescription order tracking system in accordance with an embodiment of the present disclosure.

As best shown in FIGS. 20 & 21, the storage area 30 having a plurality of bins 32 therein can also be made portable, such as by placing it on wheels or casters, thereby defining a portable prescription order distribution cart 31 that may be wheeled room-to-room throughout a healthcare facility 300 to allow easy access to and distribution of filled prescription orders.

Preferably, the portable prescription order distribution cart includes a source of power, such as a battery or the like, an input device such as a mouse and/or keyboard, and a scanning wand 500, portable tag reader 18, and monitor in communication with the computer system. The scanning wand 500 may be wired to the cart as shown in FIG. 20, or have a wireless connection to the cart as shown in FIG. 21. Accordingly, the cart serves as a stand-alone structure for allowing a worker to easily locate a particular patient's filled prescription orders within a particular bin and administer the filled prescription to the correct patient.

c. Storage Bin Locking Structure

Figure 24:
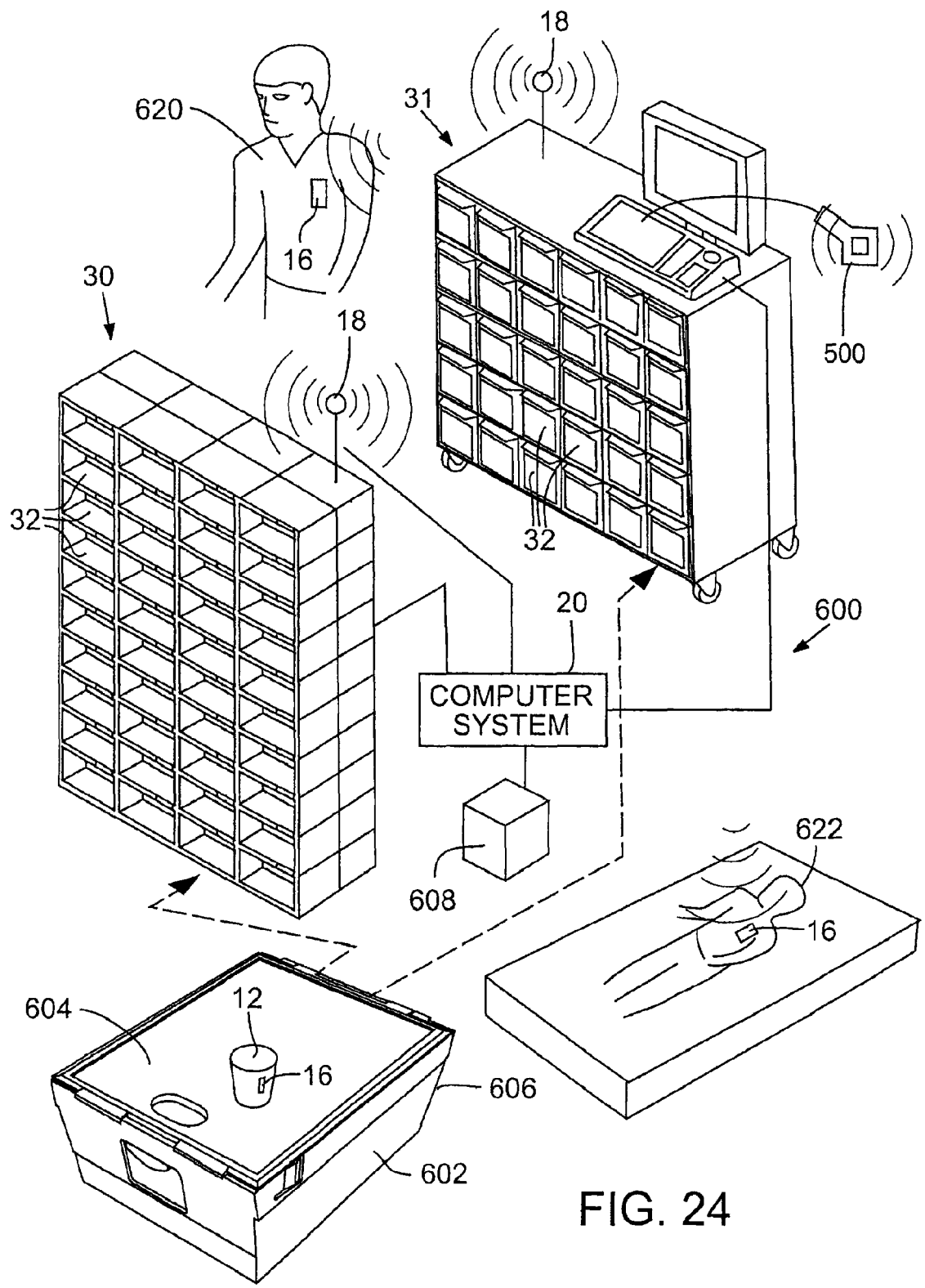
FIG. 24 is an exemplar prescription order storage cabinet locking system in accordance with an embodiment of the present disclosure.

As shown schematically in FIG. 24, each bin, either in the storage structure 30 or the cart 31 preferably includes a locking structure 600 in communication with the computer system 20 to limit access to filled prescription orders 16 placed therein. For example, a locking tray 602 can operably receive a container 604 having the filled prescription 12 thereon. The tray 602 is sized to secure the container 604 therein and to be slidably received within a bin 32. One or more hooks 606 preferably extend from the tray. The hooks 606 operably engage an electric lock 608 received within or near the bin 32 thereby locking the tray 602 within the bin 32. Accordingly, with the tray 602 locked to the lock 608 within the bin 32 and the container 604 secured within the tray 602, the container 604 cannot be removed from the bin 32.

The electric lock 608 is in communication with the computer system 20 that controls the lock 608 so as to only unlock the tray 602 from the lock 608 when predetermined criteria are met. For example, a worker 620 can wear an identification tag 16 that is detected by a tag reader 18 placed near the bin 32 in which the worker 620 seeks to unlock. The computer system 20 first verifies that the worker 620 is authorized to have access to the items the locked bin, and opens the lock 608 only if the detected worker 620 is authorized. This locking system allows commonly prescribed medications, which are often referred to in the industry as "top 100" medications, to be securely stored within a healthcare facility, but also remain easily accessible to authorized workers, particularly during times when the pharmacy serving the healthcare facility is closed.

In addition, the computer system 20 can release the lock 608 containing the filled prescription only if the patient 622 associated with the prescription order 12 is detected by a tag reader 18 positioned near the locked bin 32 containing the prescription order 12 therein. A tag worn 16 by the patient 622 or some other biometric identification system can be used by the computer system 20 to validate the patient's identity.

C. Proper Distribution Verification

Figure 23:
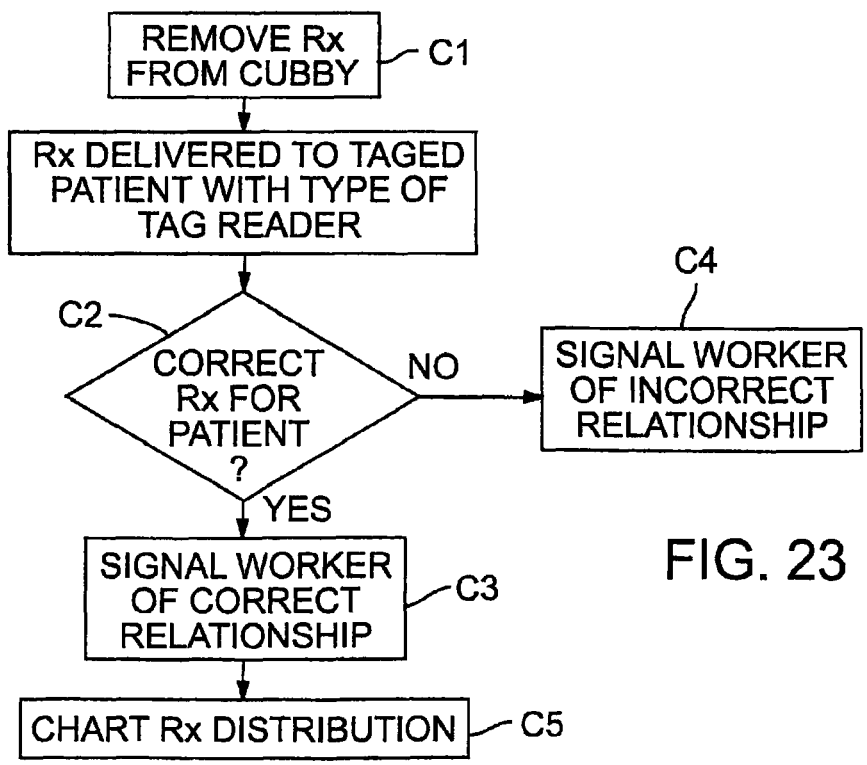
FIG. 23 is an exemplar flow chart of a possible verification system process that automatically verifies that a particular patient within a healthcare facility has been given the correct prescription order for that patient.

Preferably, unique tags are operably secured to the healthcare workers and the patients within a healthcare facility, and these tags are detected by the tag readers positioned one or near the portable cart or within each patient's room as shown in FIG. 21. Accordingly, the information collected and compiled by the computer system 20 can be used to verify that the correct prescription order of a particular patient has been dispensed to the correct patient. A block diagram of an exemplar process and application performing this function is shown in FIG. 23.

The detailed description that follows is represented largely in terms of processes and symbolic representations of operations by conventional computer components, including a processing unit, memory storage devices for the processing unit, and a display device. These operations include the manipulation of data bits by the processing unit and the maintenance of these bits within data structures resident in one or more of the memory storage devices. Such data structures impose a physical organization upon the collection of data bits stored within memory and represent specific electrical or magnetic elements. These symbolic representations are the means used by those skilled in the art of computer programming and the construction of computing devices to most effectively convey teachings and discoveries to others skilled in the art.

For purposes of this discussion, a process is generally a sequence of steps executed by a computing device leading to a desired result. These steps generally require physical manipulations of physical quantities. Usually, although not necessarily, these quantities take the form of electrical, magnetic, or optical signals capable of being stored, transferred, combined, compared, or otherwise manipulated. It is conventional for those skilled in the art to refer to these signals as bits, values, elements, symbols, characters, terms, numbers, records, files or the like. It should be kept in mind however, that these and similar terms should be associated with appropriate physical quantities for computing device operations, and that these terms are merely conventional labels applied to physical quantities that exist within and during operation of the computing device.

It should also be understood that manipulations within the computing device are often referred to in terms such as adding, comparing, moving, etc. which are often associated with manual operations performed by a human operator. The operations described herein are machine operations performed in conjunction with a human operator or user that interacts with a control device. The machines used for performing the operation of the preferred embodiment of the present disclosure, as will be understood, include a control device and other suitable input devices.

In general, in step C1, within range of a tag reader, a healthcare worker removes a prescription order from a cubby within the portable cart. The computer system detects the removal of the prescription order from the cubby and determines the patient associated with the removed prescription order. The prescription order containing a tag is delivered to a patient within range of a tag reader. In step C2, the computer system detects the tag associated with the patient and the tag associated with the prescription order and determines the identified patient is the correct patient to receive the identified prescription order. If so, transducers, such as lights or sounds, on the portable cart can operate to signal the correct relationship between the prescription order and patient (Step C3). If not, the transducers can operate, usually much more significantly, to indicate an error has been made (Step C4).

If desired, the computer system can also automatically track the time interval between the present prescription order delivery and any prior delivery of the same prescribed medication and compare this time with a predetermined time limit to alert the worker and/or patient that the medication is being administered too soon or too late. Similarly, the computer system can track all medications dispensed to a particular patient and alert a worker and/or the patient if any counter-indicated prescription order combinations have been prescribed to a particular patient.

Also, the computer system can record, or chart, the administration of the prescription order to a patient, thereby saving the healthcare worker time and avoiding the need for the pharmacy worker to manually prepare such reports or charts (Step C5).

Alternatively, the computer system can first detect the presence of a patient 622 within range of the tag reader 18 installed on the cart 31. It then consults an internal database to determine the bin in which that identified patient's prescription order is located, and it can activate one or more transducers positioned on or near that bin to alert the worker of the location of the identified patient's filled prescription order.

In cases where locking structures 600 are installed on the bins 32, the computer system 20 can automatically unlock only the bin associated with the identified patient's prescription order, thereby further preventing inadvertent distribution of an improper prescription order by the worker 620.

D. Computer System

Those skilled in the art will appreciate that an exemplary embodiment of the present disclosure relies on and incorporates several common features of modern personal computers. The general use, operation, and construction of a computer system is known and has been disclosed in numerous patients such as U.S. Pat. No. 5,818,447 to Wolf et al. and U.S. Pat. No. 5,752,025 to Shakib et al.

Referring to FIG. 6, the following discussion is intended to provide a brief, general description of a suitable computing environment in which the invention may be implemented. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

Figure 7:
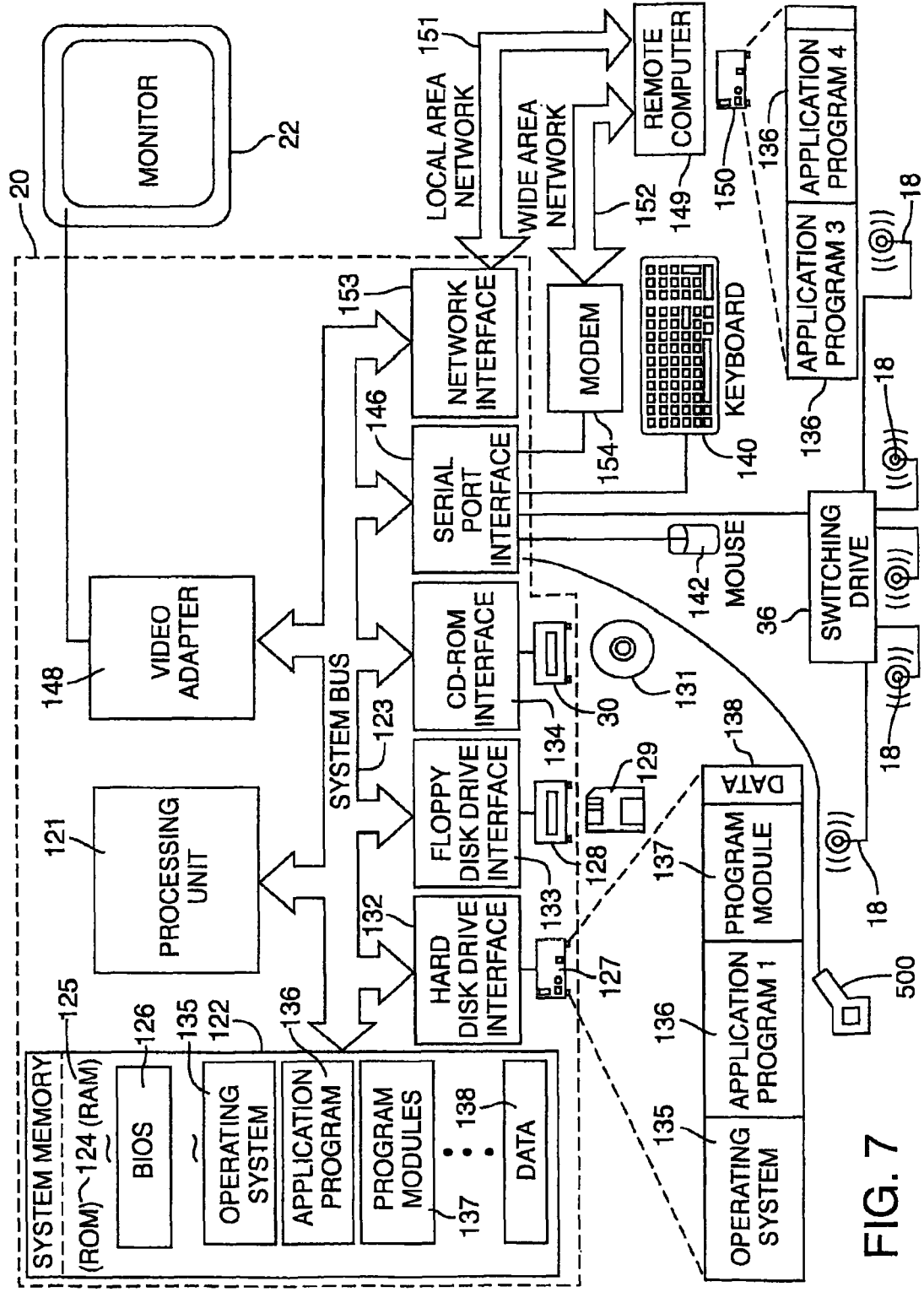
FIG. 7 is a block diagram of an exemplary computer system in accordance with a preferred embodiment of the present disclosure.

With reference to FIG. 7, an exemplary system for implementing the invention includes a general purpose computing system in the form of a conventional personal computer 20, including a processing unit 121, a system memory 122, and a system bus 123 that couples various system components including the system memory to the processing unit 121. The system bus 123 may be any of several types of bus structures including a memory bus or memory controller, a peripheral bus, and a local bus using any of a variety of bus architectures. The system memory includes read only memory (ROM) 124 and random access memory (RAM) 125. A basic input/output system 126 (BIOS), containing the basic routines that help to transfer information between elements within the personal computer 20, such as during start-up, is stored in ROM 124. The personal computer 20 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of computer readable instructions, data structures, program modules and other data for the personal computer 120. Although the exemplary environment described herein employs a hard disk, a removable magnetic disk 129 and a removable optical disk 131, it should be appreciated by those skilled in the art that other types of computer readable media which can store data that is accessible by a computer, such as magnetic cassettes, flash memory cards, digital video disk, Bernoulli cartridges, random access memories (RAMs), read only memories (ROM), and the like, may also be used in the exemplary operating environment.

A number of program modules may be stored on the hard disk, magnetic disk 129, optical disk 131, ROM 124 or RAM 125, including an operating system 135, one or more application programs 136, other program modules 137, and program data 138. A user may enter commands and information into the personal computer 20 through input devices such as a keyboard 140, pointing device 142, tag readers 18, and scanning wand 500. Other input devices (not shown) may include a microphone, joystick, game pad, satellite dish, scanner, or the like.

These and other input devices are often connected to the processing unit 121 through serial port interface 146 that is coupled to the system bus, but may be connected by other interfaces, such as a parallel port, game port or a universal serial bus (USB). A display 22 or other type of display device is also connected to the system bus 123 via an interface, such as a video adapter 148. In addition to the monitor, personal computers typically include other peripheral output devices (not shown), such as speakers and printers.

The personal computer 20 may operate in a networked environment using logical connections to one or more remote computers, such as a remote computer 149. The remote computer 149 may be another personal computer, a server, a router, a network PC, a peer device, a personal digital assistant ("PDA"), or other common network node, and typically includes many or all of the elements described above relative to the personal computer 20, although only a memory storage device 150 has been illustrated in FIG. 7. The logical connections depicted in FIG. 7 include a local area network (LAN) 151 and a wide area network (WAN) 152. Such networking environments are commonplace in offices, enterprise-wide computer networks, intranets and the Internet.

When used in a LAN networking environment, the personal computer 20 is connected to the local network 151 through a network interface or adapter 153. When used in a WAN networking environment, the personal computer 20 typically includes a modem 154 or other means for establishing communications over the wide area network 152, such as the Internet. The modem 154, which may be internal or external, is connected to the system bus 123 via the serial port interface 146. In a networked environment, program modules depicted relative to the personal computer 20, or portions thereof, may be stored in the remote memory storage device. It will be appreciated that the network connections shown are exemplary and other means of establishing a communications link between the computers may be used.

Preferably, a plurality of networked personal computers 20 are positioned within the pharmacy, one at the intake area (21, FIG. 5), one at the customer pick-up area (29, FIG. 5), and one at the data entry/label area (27, FIG. 5).

E. Multiplexing Tag Reader Array

Referring to FIGS. 5, 8-17, and 20-22, a plurality of tag readers 18, which are distributed throughout the pharmacy 14, healthcare facility, storage device and/or portable cart, are preferably integrated with a switching device 36 that periodically monitors the status of each tag reader 18 and transmits that information to the personal computer 20.

Figure 8:
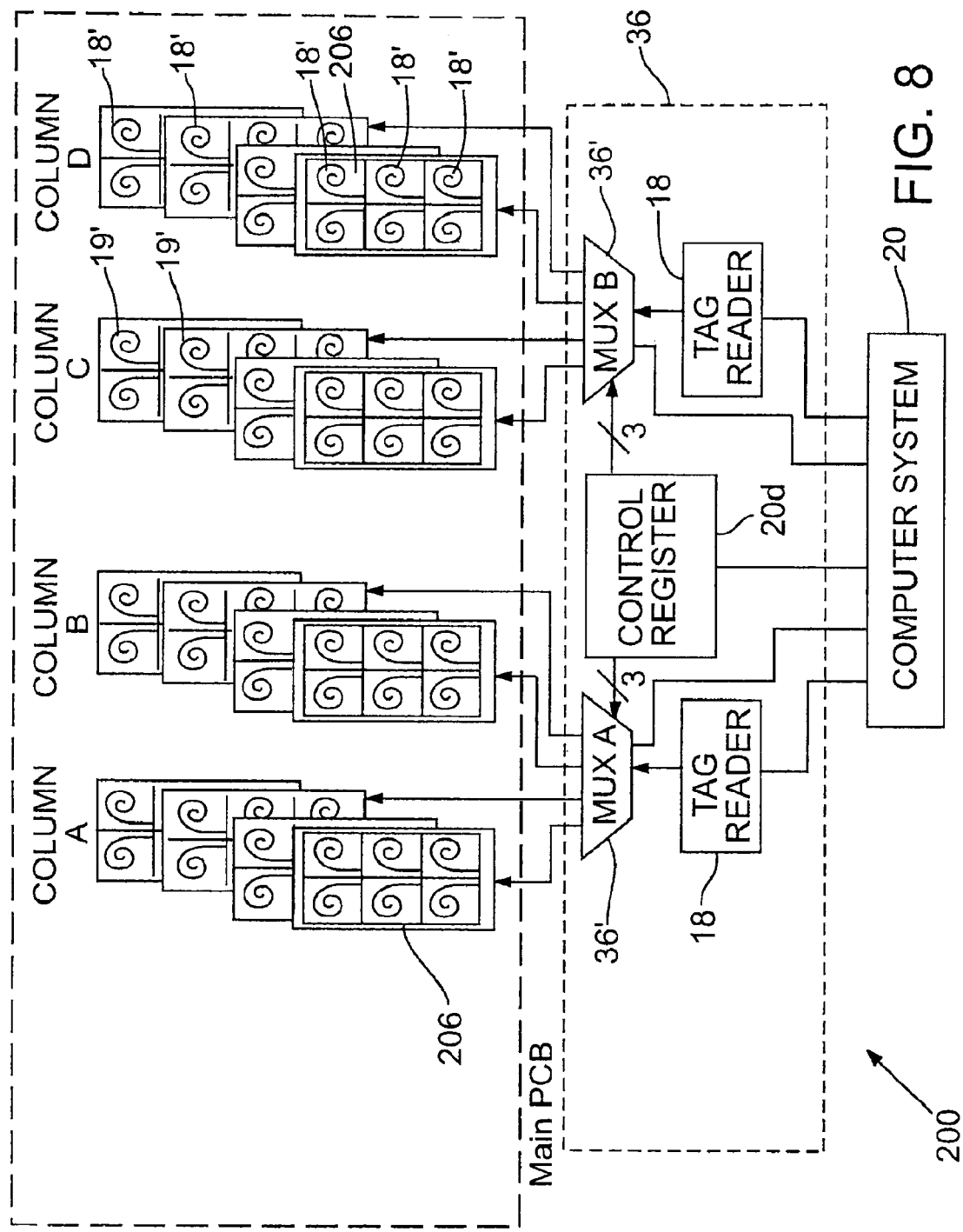
FIG. 8 is an exemplar schematic diagram of a multiplexed tag reader array and related system in accordance with an embodiment of the present disclosure.
Figure 9:
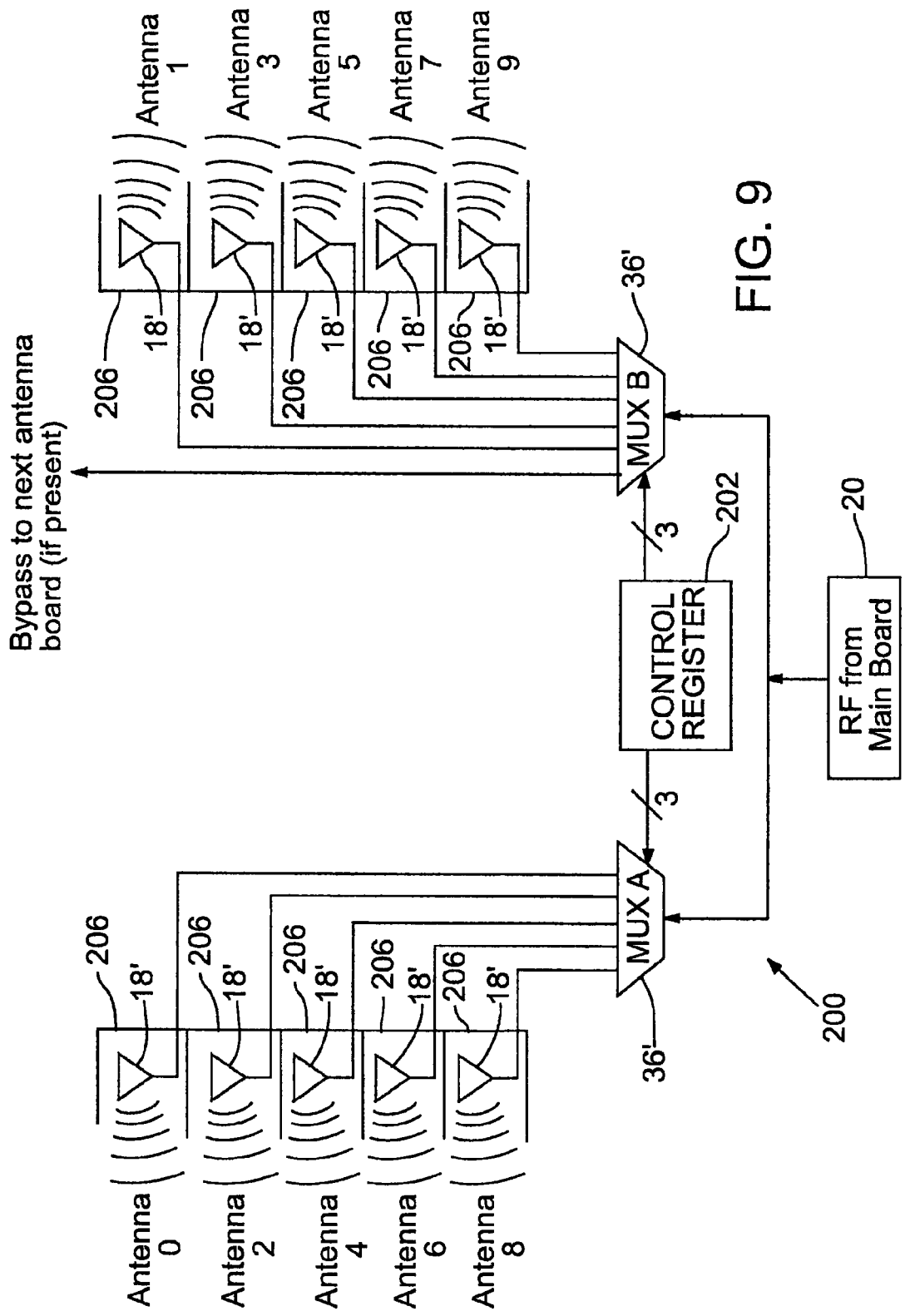
FIG. 9 is an alternative exemplar schematic diagram of a multiplexed tag reader array and related system.

An exemplar multiplexing system 200 is disclosed in FIGS. 8 & 9. Preferably, the antenna 18' of each tag reader 18 is operably secured to a multiplexer 36'. Such multiplexers 36' are commonly known to those skilled in the art. A plurality of antenna 18' are operably secured to the multiplexer 36' such that the multiplexer 36' connects each antenna 18' one-by-one to the tag reader 18. Each antenna 18' is positioned at a specific location within the pharmacy 14. For example, one or more antenna 18' can be positioned adjacent to a particular work area 97 upstream of the storage area 30, or can be positioned adjacent to a particular cubby 32 in the storage area 30. A control register 202 monitors which antenna 18' is connected to the tag reader 18 at a given time and provides this information to the computer system 20, which also detects a tracking signal from the tag reader 18 to determine the presence and a tag and thereby determine its location within the pharmacy 14.

Preferably, and as best shown in FIGS. 10-13, a plurality of antenna 18' are formed onto a substantially planar frame 204 with a signal shielding structure 206 encircling one or more antennas 18'. For example, the antenna 18' can be a coil aligned on the planar frame 204 and the signal-shielding structure 206 can be a short circuit encircling the coil on the planar frame 204. Accordingly, the interrogation field of the antenna 18' is directed substantially perpendicular to the planar frame 204. Accordingly, a large number of antenna 18' can be concentrated within a small area, say for example, in a will-call storage device, with each antenna detecting the presence of a tag only if placed within a cubby immediately adjacent to the antenna 18'. Alternatively, the shielding structure can be an electrically grounded frame that surrounds an area in which an interrogation field of a tag reader is directed.

Preferably, the tags operate at a relatively low frequency band of around 13.56 megahertz (MHz). This frequency has been found to allow a plurality of tags within a small area to each be detected by a common tag reader. Moreover, tags operating at about this frequency are able to penetrate through liquids and other materials commonly found in a pharmacy without adversely affecting the tracking performance of the tag.

Although less desirable, the tags operating at an ultra-low frequency such as in the range of about 125 kilohertz (kHz) to about 134.2 kilohertz (kHz) or in the ultra-high frequency band of between about 860 megahertz (MHz) to 960 megahertz (MHz) can also be used.

Figure 17A:
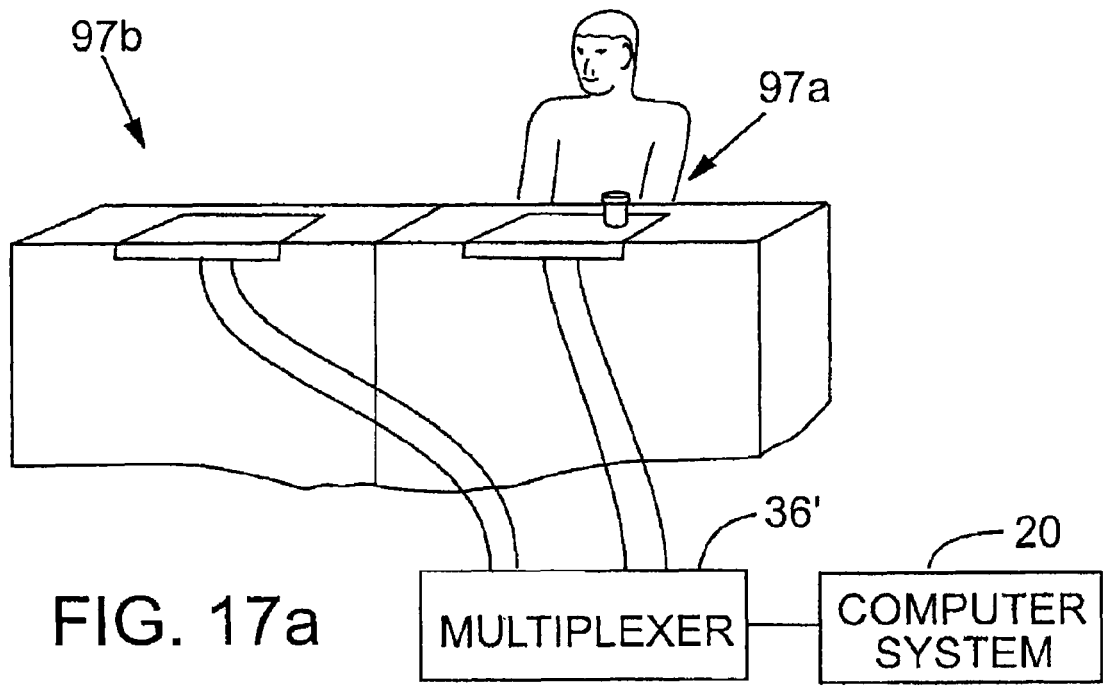
FIG. 17a is an exemplar, isometric view of a possible workstation having a substantially horizontally mounted planar frame containing at least one tag reader antenna therein.
Figure 18:
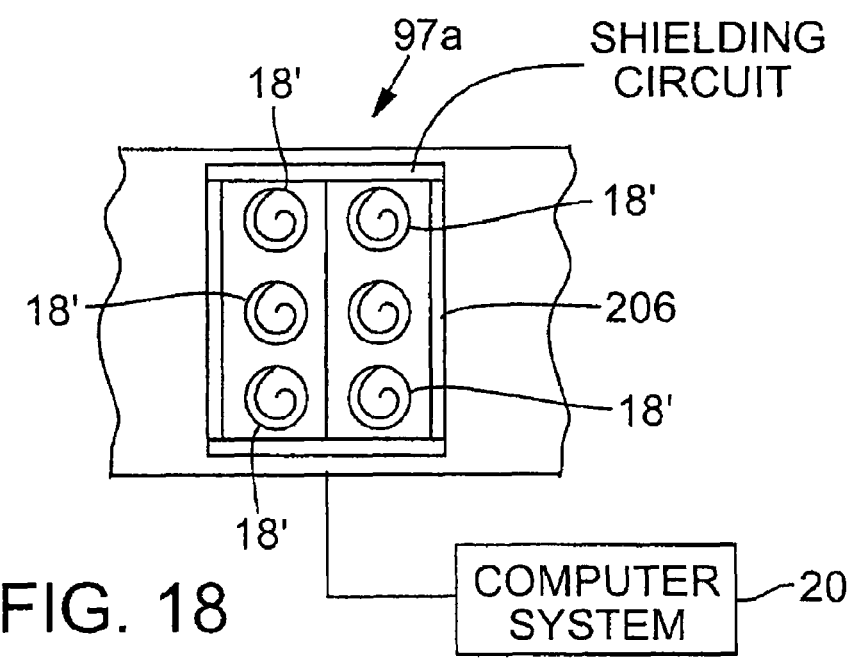

Alternatively, the planar frame 204 containing one or more antenna 18' may be positioned substantially horizontally on a work area 97a, 97b as shown in FIGS. 17a, 17b & 18 with the fields of the antenna directed substantially upward (FIG. 17a) or downward (FIG. 17b). In such case, the signal shielding structure 206 need not necessarily encircle each individual antenna 18' on the frame 204 as shown in FIG. 10. Rather, if needed the shielding structure 206 can encircle the entire frame 204 as best shown in FIG. 18 thereby defining a particular work area 97a and preventing the antenna 18' from inadvertently detecting the presence of a tag in an adjacent work area 97b.

Moreover, and referring to FIGS. 19a & 19b, a plurality of antenna can be positioned around a scanning area and all directed within that area to form a defined space or tunnel 600 in which tags placed therein are scanned by signals generated from a plurality of antenna. Such a scanning tunnel allows for more accurate detection of all tags, particularly when a plurality of tags are grouped together, such as in a bulk shipment received from a remote pharmacy or other off site location.

F. Customer Identification Verification

Figure 31:
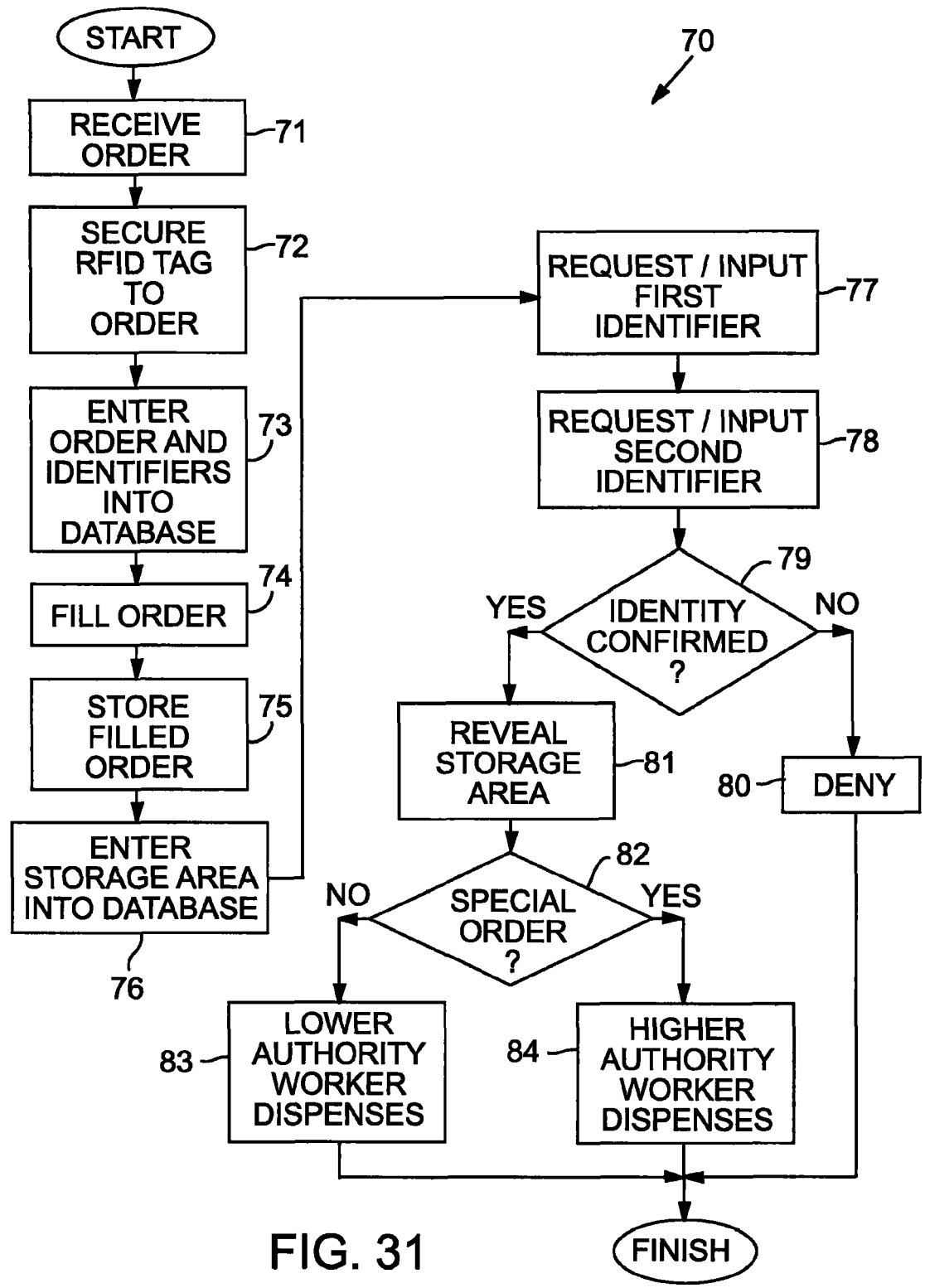
FIG. 31 is a flowchart illustrating a system and method of distributing a prescription order according to exemplary teachings of the present disclosure.

Referring now to FIG. 31, a system and method 70 of distributing a filled prescription order 12 is illustrated according to additional exemplary embodiments. As will be discussed, the method 70 helps to ensure that filled prescriptions are distributed only to the intended customer or patient. More specifically, after the prescription order 12 is placed with the pharmacy 14, the order 12 can be tracked and filled in the various ways discussed above. The location in which the filled order 12 is ultimately stored is recorded. Then, once the customer attempts to pick-up the filled order 12, the identity of the customer is confirmed using two or more customer-specific identifiers (e.g., name and password, name and date of birth, name and address, etc.). Once the customer's identity is confirmed, only then does the system inform the worker where the order 12 is currently stored. Thus, if the customer's identity cannot be confirmed, then the location of the order 12 is likely to remain hidden. On the other hand, if the customer's identity is confirmed, the location of the order 12 is revealed, and the worker can give the order 12 to the intended customer.

As shown in FIG. 31, the method 70 can begin in step 71, wherein the order 12 is received from the customer. As discussed above, the order 12 can be received at a prescription filling center 15 of a pharmacy 14. Then, in step 72, an RFID tag 16 or other unique identification can be secured to the order 12 (i.e., secured for movement with the order 12) such that the order 12 can be tracked through the pharmacy 14 during the process of filling the order 12.

Next, in step 73, the customer can provide identifying information to the pharmacy 14. For instance, in some embodiments, a pharmacy worker can inquire and record the customer's name (e.g., a first identifier) as well as the customer's date of birth, address, or unique password (e.g., a second identifier). These identifiers can be input by the worker using the keyboard 120 of the computer system 20. In other embodiments, the customer can input the identifiers, for instance, using the keyboard 120 so that the worker remains unaware of the identifiers. These identifiers can then be saved in memory (i.e., first and second saved identifiers) within the computer system 20. It will be appreciated that the identifiers can be of any suitable type for identifying the customer other than those listed above. It will also be appreciated that there can be any number of two or more identifiers that are taken in step 73.

Then, in step 74, the order 12 can be filled. As discussed above, the order 12 can be filled by moving along a workstream through the pharmacy 14. Also, the location of the order 12 can be tracked as it moves through the pharmacy 14 and as it is filled, for instance, using one or more tag readers 18 positioned throughout the pharmacy 14. The location of the order 12 can be tracked automatically using radio communications (e.g., RFID tracking) that are communicated and saved in memory in the computer system 20. The location of the order 12 can also be tracked using manual means (e.g., scanning of barcodes by the workers, etc.).

Once the order 12 is filled, the order 12 can be placed in storage (i.e., placed in its respective storage area) (step 75). As discussed above, the filled order 12 can be placed within a respective one of the cubbies 32 of the storage bin 30 (FIG. 5). Then, in step 76, the storage area can be saved in memory within the computer system 20. The storage area can be saved in the same database containing the identifiers entered in step 73 such that the storage area and the identifiers are associated together. In some embodiments discussed above, the storage area can be automatically detected using tag readers 18 positioned at the respective cubby 32 (FIG. 5). In other embodiments, the worker can manually place the order 12 in one of the cubbies 32 and manually enter the particular cubby 32 into memory and/or utilize a barcode system to record the storage area of the order 12.

It will be appreciated that soon after the order 12 is placed in storage, the worker is likely to forget where the order 12 is located because the order 12 is likely to be arranged among a large number of other orders. The orders 12 need not be alphabetized or otherwise organized. Instead, the orders 12 can be placed in any available cubby 32. The worker can rely on the information saved in the database for locating the order 12 when the customer comes to pick up the order 12.

Specifically, in step 77, when the customer comes back to the pharmacy 14 to pick up the order 12, the customer provides a requested first identifier (i.e., first requested identifier). Likewise, in step 78, the customer provides a requested second identifier (i.e., second requested identifier). The customer will attempt to provide the identifiers provided in step 73. Thus, in some embodiments, the worker can ask the customer his or her name (first identifier) and address, date of birth, or passcode (second identifier), and the worker can input this information into the computer system 20 using the keyboard 120. In other embodiments, the customer can input the identifiers using the keyboard 120.

Then, in decision block 79, it is determined whether the identity of the customer is confirmed. The identity of the customer is confirmed (i.e., block 79 answered affirmatively) if the first and second identifiers requested in steps 77 and 78 correspond satisfactorily (e.g., match exactly) with the identifiers gathered in step 73. If the identifiers requested in steps 77 and 78 do not match or otherwise correspond, then the customer's identification remains unconfirmed (i.e., block 79 answered negatively).

If the customer's identity remains unconfirmed, step 80 follows, and the customer is denied the ability to pick up the order 12. This is because the worker is most likely unaware of the location of the filled order 12. However, if the customer's identity is confirmed, step 81 follows, and the storage area of the order 12 saved in step 76 is revealed to the pharmacy worker. As discussed above, the transducer 17 can emit a light, change a color of a light, can emit a sound, the display 22 of the computer system 20 can display the storage area, etc. in step 81. Also, the cubby 32 containing the order 12 can be automatically opened or unlocked to reveal the storage area of the order 12. Thereafter, the order 12 can be located by the worker and transferred to the customer.

In the embodiment shown, the orders 12 can be prioritized or segregated in various ways. For instance, some orders 12 (e.g., highly addictive painkillers, highly hazardous chemicals, etc.) can be distinguished as "special," and extra security measures can be taken to ensure that these orders 12 are transferred to the intended customer. Thus, as shown in decision block 82 of FIG. 31, it is determined whether the order 12 is "special." If it is not a "special" order 12, then a lower authority pharmacy worker can transfer the order 12 to the customer (step 83). However, if the order 12 is a "special" order 12, then the higher authority pharmacy worker can transfer the order 12 to the customer (step 84) instead of the lower authority worker. It will be appreciated that the orders 12 can be segregated in any suitable fashion into any number of categories. It will also be appreciated that the lower authority workers can be those without a pharmacy degree, without security clearance, etc. The higher authority workers can be those with a pharmacy degree, security clearance, etc.

Accordingly, the method 70 can ensure that the orders 12 are transferred to intended customers. The method 70 can be employed in a traditional pharmacy 14 or using a portable prescription distribution cart of the types discussed above, or in any other suitable prescription distribution center. Also, the "customer" discussed above can be the actual patient that will be taking the prescriptions, or the "customer" can be one that places the order 12 and/or picks up the order 12 on behalf of that patient. In either case, the prescriptions are likely to be taken by the intended patient instead of being inadvertently re-routed. Moreover, the customer identifiers taken in step 73 can be permanently stored in the database as a customer profile such that the customer need not provide new identifiers every time the customer places a new order 12 and/or attempts to get a prescription order 12 refilled. In this regard, every time the order 12 is filled, the filled order 12 can be tracked through the pharmacy 14 and the storage area for that filled order 12 can be associated with the customer identifiers previously saved within the database.

G. Transfer of Filled Prescription from Pharmacy to Customer

Figure 32:
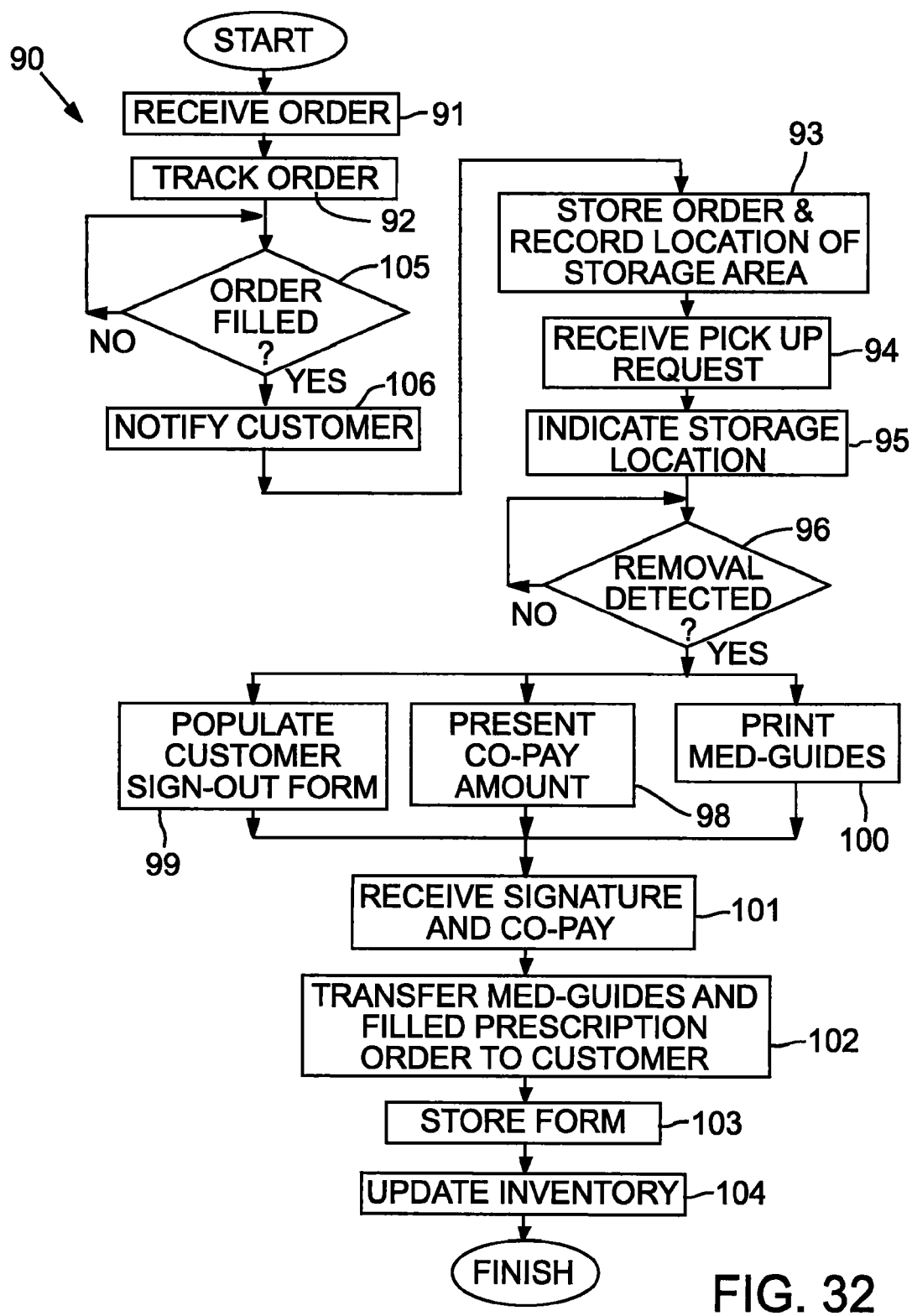
FIG. 32 is a flowchart illustrating a method of tracking, filling, and storing a prescription order and automatically generating transaction information to facilitate dispensing of the prescription order to the customer.

Referring now to FIG. 32, a method 90 will be discussed for filling a prescription order 12 and ultimately transferring the filled prescription order 12 to the customer. As will be discussed, this method 90 can be at least partially automated. Accordingly, this transaction can be facilitated and expedited. Also, inventories of the filled prescription orders 12 can be automatically updated for greater inventory accuracy.

The method 90 can be employed, for example, in the pharmacy 14 represented in FIG. 5. As mentioned above, the prescription order 12 can be received at location 21 (i.e., incoming transaction location), then filled at locations 23, 24, 25, 27, and/or 28. Subsequently, the filled order 12 can be stored at location 30, within one of the cubbies or bins 32. Also, the customer can pick up the filled prescription order 12, pay for the prescription order 12, and/or receive information about the filled prescription order at location 29 (i.e., outgoing transaction location). As discussed above, the location of the prescription order 12 within the pharmacy 14 can be tracked and recorded within the computer system 20.

Also, as discussed above, the computer system 20 can include one or more terminals (e.g., one or more desktop computers, laptop computers, handheld computerized devices, or other type of computer). The computer system 20 can include many features of a conventional computer system, such as a CPU, a display (monitor) 22, a keyboard 140, a mouse, or other input devices. The computer system 20 can also include a memory device (e.g., ROM). At least some components of the computer system 20 can be located on or adjacent to one or more of the locations 21, 23, 24, 25, 27, 28, 30 to be accessible to the pharmacy worker and/or the customer.

Figure 33:
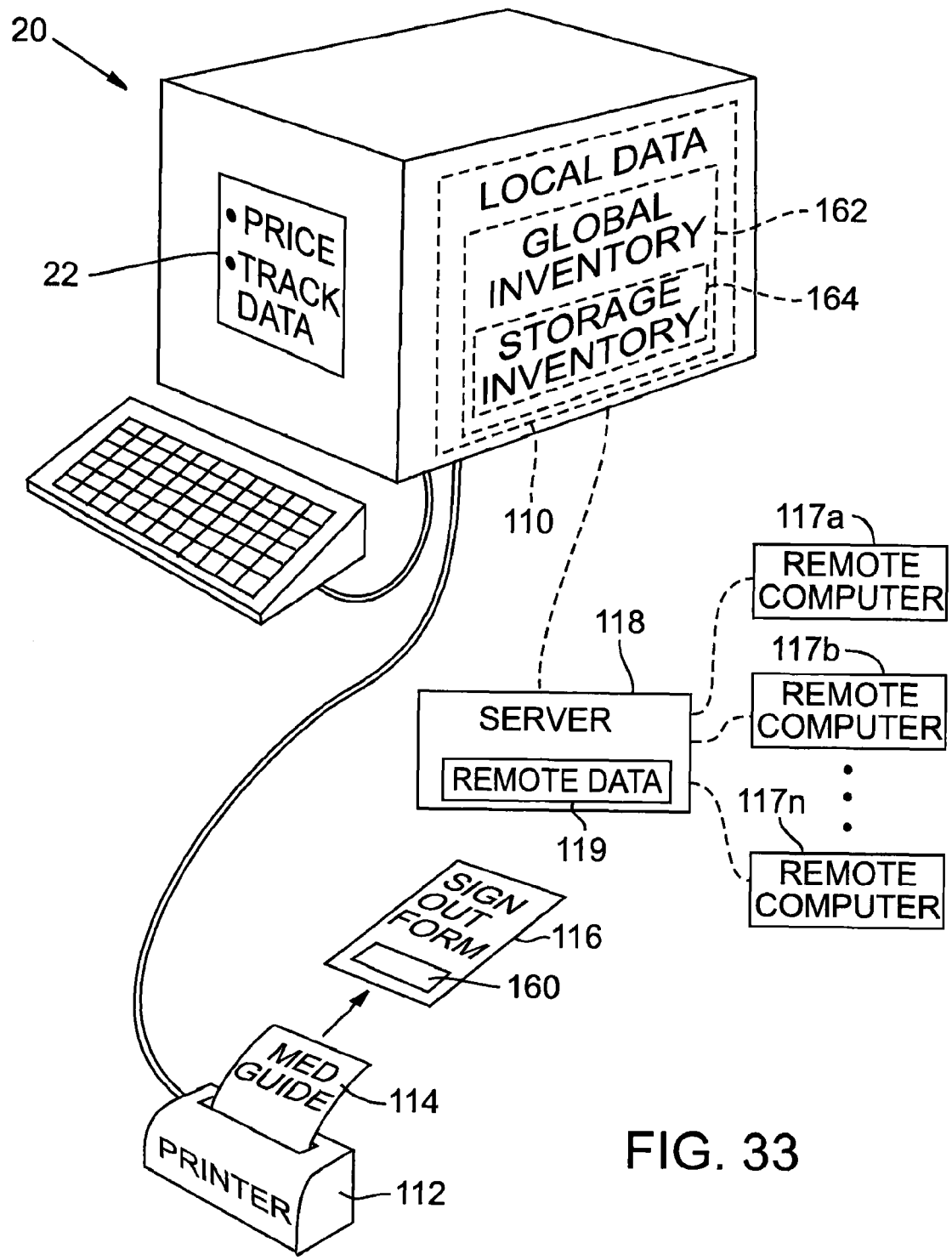
FIG. 33 is a schematic illustration of a computer system within a pharmacy and that can be used in connection with the method of FIG. 32.

As shown in FIG. 33, the memory device of the computer system 20 can include at least one local database 110 stored thereon. The local database 110 can include a variety of information relating to the customers of the pharmacy 14 and corresponding information about their prescription orders 12 (e.g., customer names, customer contact information, such as addresses, phone numbers, e-mail addresses, and fax numbers, customer passwords and/or other identifiers, doctor information, type and quantity of prescriptions for each customer, NDC numbers, quantity of pills for each NDC number within each bottle, etc.). The database 110 can also include tracking information about each prescription order (e.g., the location of the prescription order 12 within the pharmacy and/or the particular bin 32 where each filled prescription order 12 is stored within the storage area 30). Also, in some embodiments, the database 110 can include insurance information (e.g., co-pay amounts for particular prescriptions for particular customers, other insurance information, etc.) for the filled prescription orders.

The database 110 can additionally include one or more inventories 162, 164. For instance, the database 110 can include a global inventory 162 (pharmacy management system), which can be an electronic record of the quantity of each item (drug, device, pharmacy product, etc.) within the pharmacy 14. Thus, the global inventory 162 can include quantities of each item with an associated NDC number, numbers of individual pills, etc. The database 110 can additionally include a storage inventory 164, which can be an electronic record of the filled prescription orders 12 within the storage area 30 (e.g., quantities of each prescription medication and the associated NDC numbers, number of individual pills, etc. within each filled prescription order 12 in the storage area 30). Also, it will be appreciated that the storage inventory 164 can also include tracking information about the filled prescription orders 12. For instance, the storage inventory 164 can record the type and quantity of drugs and/or devices within each filled prescription order 12, the associated customer information, and the particular storage bins 32 in which the particular filled prescription orders 12 are stored. The inventories 162, 164 can include additional information about the items, such as the cash price for the items, the co-pay amounts for each particular order 12, etc.

It will be appreciated that the items inventoried within the global inventory 162 can encompass and include those drugs/devices included in the filled prescription orders 12 within the storage area 30. In other words, the items inventoried within the global inventory 162 can include those items associated with the filled prescription orders 12 stored in the storage area 30. For example, the pharmacy 14 might have twenty Oxycodone pills on-site, and ten of that twenty might be included in a particular filled prescription order 12 in a particular storage bin 32. Therefore, the global inventory 162 would show that there are twenty Oxycodone pills on-site, and the storage inventory 164 would show that there are ten Oxycodone pills in the particular storage bin 32.

The global and storage inventories 162, 164 can be linked. As such, updating one inventory 162, 164 can automatically update the other inventory 162, 164 as will be discussed in greater detail below.

Moreover, the computer system 20 can be one of several different remote computers 117a, 117b, 117n within a computerized network as shown in FIG. 33. The computer system 20 and the remote computers 117a, 117b, 117n can each be in communication with a remote server 118. In some embodiments, the computerized network can be employed for connecting computer systems 20 within a chain of pharmacies at different locations. The computer system 20 can access a remote database 119. The remote database 119 can be centralized on the server 118, or the remote database 119 can be located on one of the remote computers 117a, 117b, 117n. The remote database 119 can be linked to the local database 110 in some embodiments such that changing data in one database 110, 119 will automatically update the other database 110, 119. Also, the remote database 119 can be used instead of a local database 110. As such, the remote database 119 can be used for storing any of the data described above in relation to the local database 110.

In addition, the computer system 20 can be in communication with external devices, such as a printer 112, which prints hard copies of various documents 114, 116 necessary for completing transactions with customers as will be discussed. For instance, the printer 112 can print hard copies of Medication Guides 114 (Med-Guides). It will be appreciated that FDA may require Medication Guides 114 to be given to the customer along with the filled prescription order 12. The guides 114 address issues that are specific to particular drugs and drug classes, and they contain FDA-approved information that can help patients avoid serious adverse events. Thus the Medication Guides 114 can include the name of the prescription, side effects of using the prescription, drug interaction information, etc. The Medication Guides 114 can be stored electronically on one or both of the databases 110, 119.

The printer 112 can also print out receipts and/or sign-out form(s) 116. The form 116 can include a variety of information, including customer information (e.g., customer name, etc.). Also, the form 116 can include a signature area 160. As will be discussed, the customer can sign within the signature area 160 to signify that the filled prescription order 12 has been transferred to the customer. Then, the form 116 can be stored by the pharmacy to be used as proof that the customer picked up and received the prescription order 12. In some embodiments, the form 116 can also include receipt information (e.g., cost or co-pay amount, change received, etc.), and the customer can receive a copy of the form 116. Also, in some embodiments, the form 116 can be an electronic form, which is displayed electronically on the display 22, and the electronic form 116 is used in addition to or instead of the hard copy printed by the printer 112. To sign the electronic version of the form 116, the customer can use a stylus that is detected by a touch sensitive reader (not shown). In some embodiments, the electronic version of the form 116 can be presented to the customer for signature, and the form 116 can be saved on the database 110, 119. In some embodiments, electronic templates for the form 116 can be stored on one or both databases 110, 119.

It will be appreciated that the computer system 20 can be used as a cash register as well. Thus, the computer system 20 can be used to calculate or otherwise obtain a sale price for the filled prescription order 12. This price can be displayed on the display 22. There can also be an associated cash box or drawer used for storing cash, checks, or other payment for the filled prescription order 12. Moreover, the computer system 20 can also include one or more devices, such a credit or debit card reader, for completing sale of the filled prescription order 12.

As discussed above, the pharmacy 14 can include a tracking system for tracking the location of the prescription orders 12 throughout. For instance, each prescription order 12 can include a respective identification tag 16, and there can be a number of tag readers 18 positioned throughout the pharmacy 14. Tag readers 18 can be included within respective storage bins 32 as well so that the particular location within the storage area 30 can be tracked and saved (e.g., within the local database 110). Thus, the location and status of each prescription order can be tracked along a workflow within the pharmacy 14, e.g., from location 21 (FIG. 5), where the order 12 is received, to location 29, where the filled prescription order 12 is transferred to the customer.

Referring specifically to FIG. 32, the method 90 of receiving, filling, and transfer of the filled prescription order will be discussed. The method can begin in block 91, wherein the prescription order is received. The order can be received directly at location 21 (FIG. 5), over the phone, by fax machine, by e-mail, or via any other means.

Subsequently, as shown in block 92 in FIG. 32, the prescription order can be moved along the workflow within the pharmacy to ultimately fill the prescription order 12, and the order 12 can be tracked during the filling process. The location and status of the prescription order can be tracked through the pharmacy 14 as discussed above (e.g., using the RFID tags 16 located on the prescription orders 12 and using the RFID tag readers 18 located throughout the pharmacy 14).

Next, it is determined whether the order is available for pickup by the customer (i.e., is available to be transferred from the pharmacy to the customer). This determination can be made in several ways. In the embodiments illustrated in FIG. 32, this determination is made at block 105 by the computer system 20 by tracking the order 12 and detecting that the order 12 has reached a predetermined location within the pharmacy 10 (e.g., detecting that the order 12 has been deposited in one of the storage bins 32 within the storage area 30). Detecting that the prescription order 12 has been filled (i.e., decision block 105 answered affirmatively) can occur in other ways as well, such as by manually pressing a button, clicking a mouse, scanning an ID card, or otherwise manually inputting a command to the computer system 20 (e.g., after the filled prescription order 12 has been checked and verified, but before being placed into storage). The method 90 can loop back to decision block 105 until the prescription order 12 has been filled.

Upon detecting that the prescription order 12 has been filled, the method 90 can trigger one or more processes automatically, and those processes can facilitate the transfer of the prescription order 12 from the pharmacy to the customer. In the embodiments illustrated, these processes are illustrated at blocks 106, 98, 99, and 100, each of which will be discussed in detail. Other processes can also be automatically triggered, such as automatic updating of the storage inventory 164 and/or the global inventory 162 (block 104), which will be discussed.

In the embodiments of FIG. 32, block 106 can follow an affirmative result of block 105. Specifically, in block 106, the computer system 106 can automatically notify the customer that the filled prescription order is available for transfer from the pharmacy to the customer. For instance, the computer system 106 can access one of the databases 110, 119 to obtain the respective customer's contact information (phone number, e-mail address, fax number), and can the system 20 can send an automated message to the customer according to that contact information.

Next, the filled prescription order 12 can be placed in storage as shown in block 93. Also, as discussed above, the exact storage bin 32 can be tracked and recorded (e.g., in the local database 110) such that the pharmacy worker can quickly, conveniently, and accurately locate the filled prescription order when necessary. It will be appreciated that in some embodiments, depositing the filled prescription order 12 into storage can be at least one indication that the prescription order 12 has been filled and is ready for pickup, and then the customer notification is automatically sent (block 106).

The method 90 continues when the customer requests pickup of the filled prescription order 12, as represented in block 94. For instance, the location 29 (transaction area) can include a will-call or pick-up window where the customer can make such a request to the pharmacy worker. As discussed above, once the request has been made (and the customer has supplied his or her unique identifiers), the computer system 20 can reveal the exact storage bin 32 of the customer's filled prescription order, as represented in block 95.

Next, in decision block 96, it can be determined whether the order 12 has been removed from the storage bin 32. This determination can be made based on the signals provided by a sensor within the storage area. For instance, the RFID tag 16 on the filled prescription order 12 and the RFID reader 18 on the storage bin 32 can communicate to detect removal of the filled prescription order from its storage bin 32. Other sensors can be used as well. For instance, the storage bin 32 can include electrical terminals and the filled prescription order 12 can include corresponding electrical terminals, and when the filled prescription order 12 is removed, the electrical terminals can be disconnected to detect removal.

The determination of block 96 can be another indication (or the only indication) that the prescription order 12 is ready and available for transfer to the customer. Once removal of the filled prescription order 12 has been detected (decision block 96 answered affirmatively), then the method 90 continues by automatically generating transaction information that can facilitate and expedite the transfer of the filled prescription order 12 to the customer as represented in blocks 98, 99, and 100.

For instance, as shown in block 98, the computer system 20 can automatically present a sale price for the filled prescription order 12. The sale price can be a co-pay amount if the customer has prescription insurance coverage for the order 12, the sale price can be a full cash value if the customer has no prescription insurance coverage for the order 12, etc. In some embodiments, the sale price has been previously calculated and stored in memory in the local and/or remote database 110, 119 (i.e., within one or both inventories 162, 164). Thus, block 98 includes accessing the database(s) 110, 119 to obtain the pre-calculated sale price and displaying that price on the display 22 to the customer. In other embodiments, the sale price has not been pre-calculated, and the system 20 can thus access the local and/or remote database 110, 119 to then calculate and determine the particular sale price for the filled prescription order 12. For example, the database(s) 110, 119 can include stored insurance and co-pay information for the particular customer, and the system can calculate the co-pay for the particular prescription order 12, or the database(s) 110, 119 can include a price list and the system can calculate the full sale price accordingly. Once calculated, the system 20 can control the display 22 to display the price to the customer.

Moreover, as shown in block 99, the computer system 20 can generate the sign-out form 116. For instance, the system 20 can access the local and/or remote database 110, 119 to find the correct template for the electronic form 116 and to find stored customer information to include on the form 116. Specifically, the system 20 can populate the template by adding the customer's name, address, prescription name, and/or other information thereto. Accordingly, the system 20 can automatically customize the form 116 for the particular customer and can leave the signature area 160 blank. Once customized, the form 116 can be presented to the customer in hard copy or electronic form for signature.

Additionally, as shown in block 100, the computer system 20 can automatically access the database(s) 110, 119 to obtain the appropriate Medication Guide(s) 114 or other medical information relating to the filled prescription order 12. Once found, the system 20 can automatically generate (print) those Medication Guides and/or other medical information. It will be appreciated that system 20 can print to a printer 112 located at location 29 (FIG. 5) so that the Medication Guide(s) 114 and/or the sign-out form 116 can be easily accessible at pick-up.

Next, in block 101, the customer can sign the form 116 and pay for the filled prescription order 112, and the signature and payment can be received by the pharmacy. Then, in block 102, the filled prescription order 12 and Med-guide(s) 114 can be transferred to the customer.

Then, in block 103, the executed form 116 can be stored. If the form 116 was presented and signed as a hard copy, the form 116 can be manually filed. Also, if the form 116 was presented and signed in an electronic format, the computer system 20 can automatically save the executed form 116 in memory in one or both databases 110, 119. Moreover, the form 116 can be scanned and saved in memory in the database(s) 110, 119.

Finally, in block 104, the computer system 20 can automatically update the storage inventory 164 and/or the global inventory 162. For instance, the computer system 20 can update the storage inventory 164 to record that the prescription order 12 has been removed from the corresponding bin 32 and to reflect that the bin 32 is now empty and to reflect that the prescription order 12 has been transferred to the customer. This can cause the computer system 20 to automatically update the global inventory 164 in a similar fashion such that the quantities of drugs and/or devices inventoried in the global inventory 164 can be updated. The system 20 can also save information about the transaction, such as the time the order 12 was picked up by the customer, the name of the pharmacy worker that conducted the transaction, etc.

It will be appreciated that the storage inventory 164 can also be used for recording how long filled prescription orders 12 have been waiting for pickup by the customer. For instance, the pharmacy worker can query the computer system 20 and the storage inventory 164 to identify each of the filled prescription orders 12 that have been available (but unsold) for a predetermined time (e.g., all of the filled prescription orders 12 that have been available for 10 days or more). The system 20 can identify the particular storage bin 32 for each of these older filled prescription orders 12. With this knowledge, the worker can clear those bins 32 and return those filled prescription orders 12 to stock. Also, the global inventory 162 can be automatically updated to reflect that the drugs and/or devices contained in those filled prescription orders 12 have been returned to stock.

Moreover, in some embodiments, the system 20 can identify those filled prescription orders 12 that have remained in storage for a predetermined amount of time (e.g., 10 days or more), and the system 20 can be used to re-notify the particular customer that their filled prescription order 12 is available for pickup. For instance, the system 20 can automatically perform this check according to a predetermined schedule, and the system 20 can automatically send out notifications to customers as needed. Also, a pharmacy worker can perform this check manually (e.g., by entering commands to identify all older filled prescription orders 12), and the pharmacy worker can then send out customer notifications (e.g., by entering commands to transmit the notifications to the customers).

Additionally, it will be appreciated that certain aspects of the method 90 can be employed in situations where the prescription order 12 is filled off-site and placed into the storage area 30. For instance, this type of filled prescription order 12 can be assigned a RFID tag 16 and incorporated into the system 20 for tracking. The global inventory 162 can be updated to include the drugs/devices in the filled prescription order 12 therein. Then, tracking of the filled prescription order 12 can begin once the filled prescription order 12 is placed into a particular storage bin 32, and the storage inventory 164 can be updated accordingly. Placement of the filled prescription order 12 into storage can then trigger auto-notification of the customer (block 106). Subsequently, once the customer requests pickup of the order 12 and the filled prescription order 12 is removed from its storage bin 32, the form 116 can be populated (block 99), the co-pay amount can be calculated (block 98), the Medical Guides can be printed (block 100), etc.

Accordingly, the method 90 can be useful for facilitating and expediting sale or other transfer of the prescription order 12 to the customer. For instance, the customer can be automatically notified once the order 12 is ready for pickup, thereby making the pharmacy operate more efficiently. Also, the Medical Guides 114, sign-out forms 116, co-pay information, and/or other transaction information can be automatically generated, for instance, as soon as the pharmacy worker removes the prescription order 12 from the correct bin 32. Thus, the customer can receive the prescription order 12 more quickly, and the pharmacy worker can save time generating the forms 116, Medical Guides 114, calculating costs, etc. Moreover, the inventories 162, 164 and other records can be accurately and conveniently maintained.

H. Conclusion

In view of the wide variety of embodiments of the present disclosure, it should be apparent that the detailed embodiments are illustrative only and should not be taken as limiting the scope of the present disclosure. For example, although the preferred tags have a read-write feature, a less complex "read-only" tag may also be used in some situations. For example, the computer system can correlate a particular "read only" code on a tag with one or more aspects of the prescription order and/or person to which it is associated with, and use this correlation throughout the tracking system. Furthermore, the transaction information (Medical Guides 114, sign-out forms 116, co-pay information, etc.) can be automatically generated upon any event other than the removal of the prescription order 12 from the corresponding bin 32. Rather, the present disclosure includes all such modifications as may come within the scope of the following claims and equivalents thereto.

We claim:

1. A method of conducting a transaction involving transfer of a filled prescription order from a pharmacy to a customer, the method comprising:
    a computer system automatically detecting that a filled prescription order is available for transfer from the pharmacy to the customer by the computer system detecting the presence of the filled prescription in a pharmacy storage area and automatically correlating the filled prescription with the customer; and
    upon detection that the filled prescription order is available for transfer from the pharmacy to the customer, at least one of:
        automatically notifying the customer that the filled prescription order is available for transfer from the pharmacy to the customer,
        automatically populating a form with at least one piece of customer information, the form intended for signature by the customer to signify transfer of the filled prescription order from the pharmacy to the customer,
        automatically providing a sale price for the filled prescription order,
        automatically providing information about the filled prescription order, and
        automatically updating an inventory of filled prescription orders stored within the pharmacy.

2. The method of claim 1, further comprising accessing a database to obtain stored information.

3. The method of claim 2, wherein accessing the database includes accessing the database to obtain stored customer contact information, and wherein automatically notifying the customer includes transmitting notification according to the stored customer contact information.

4. The method of claim 2, wherein accessing the database includes accessing the database to obtain stored customer information, and wherein automatically populating the form includes automatically populating the form with the stored customer information.

5. The method of claim 2, wherein accessing the database includes accessing the database to obtain stored customer insurance information, and wherein automatically providing the sale price includes providing the sale price according to the stored customer insurance information.

6. The method of claim 2, wherein accessing the database includes accessing the database to obtain the medical information stored thereon, and wherein automatically providing medical information includes generating a hard copy of the medical information.

7. The method of claim 2, wherein accessing the database includes accessing a local database that is local to the pharmacy.

8. The method of claim 2, wherein accessing the database includes communicating with a remote database within a computerized network.

9. The method of claim 1, wherein automatically updating the inventory includes subtracting the filled prescription order from the inventory of filled prescription orders stored within the pharmacy.

10. The method of claim 9, further comprising automatically updating a global inventory, which records a quantity of items within the pharmacy including items associated with the filled prescription orders stored within the pharmacy, upon subtracting the filled prescription order from the inventory of filled prescription orders stored within the pharmacy.

11. The method of claim 1, wherein detecting that the filled prescription order is available for transfer from the pharmacy to the customer includes detecting removal of the filled prescription order from a storage area.

12. The method of claim 1, wherein detecting that the filled prescription order is available for transfer from the pharmacy to the customer includes deposit of the filled prescription order into a storage area.

13. The method of claim 1, further comprising receiving a prescription order that becomes the filled prescription order, moving the prescription order along a workflow stream by moving the prescription order by hand between a plurality of physically spaced apart locations to manually fill the prescription order, and automatically tracking the prescription order within the pharmacy as the prescription order moves along the workflow stream to become the filled prescription order.

14. The method of claim 13, wherein the pharmacy includes a storage area having a plurality of compartments, and wherein automatically tracking the prescription order includes automatically tracking which of the plurality of compartments in which the filled prescription order is stored.

15. The method of claim 13, wherein automatically tracking the prescription order includes automatically tracking the prescription order with a tracking system, the tracking system including a tag that is secured for movement with the prescription order, the tracking system also including a tag reader that tracks the location of the tag to thereby track the location of the prescription order.

16. A method of conducting a transaction involving transfer of a filled prescription order a pharmacy to a customer, the method comprising:
receiving the prescription order at a first location upstream of the storage area;
operably securing the tag to the prescription order upstream of the storage area, the tag having a unique identifier that is machine-readable by a first location tag reader in proximity to the tag regardless of the orientation of the tag relative to the first tag reader;
associating the unique identifier of the tag with the first and second saved identifiers in a computer system, the computer system including a computer-readable memory device;
moving the prescription order by hand to a second location within the pharmacy for manual filling upstream of the storage area, the second location having a second location tag reader in communication with the computer system;
automatically detecting the presence of the prescription order at the second location by reading the unique identifier of the tag with the second location tag reader regardless of the orientation of the tag and automatically recording in the computer system the location of the prescription order at the second location for the manual filling;
moving the filled prescription order along a workflow stream by moving the prescription order by hand between a plurality of physically spaced apart locations to manually fill the prescription order;
moving the filled prescription order by hand to the storage area defined by the one of an array of compartments, each compartment having a corresponding compartment tag reader that is in communication with the computer system and is operable to read the unique identifier of the tag on the filled prescription order regardless of the orientation of the tag,
automatically tracking the prescription order within the pharmacy as the prescription order moves along the workflow stream to become a filled prescription order and automatically tracking which of the plurality of compartments in which the filled prescription order is stored;
detecting that a filled prescription order is available for transfer from the pharmacy to the customer; and
upon detection that the filled prescription order available for transfer from the pharmacy to the customer, at least one of:
automatically notifying the customer that the filled prescription order is available for transfer from the pharmacy to the customer,
automatically populating a form with at least one piece of customer information, the form intended for signature by the customer to signify transfer of the filled prescription order from the pharmacy to the customer,
automatically providing a sale price for the filled prescription order,
automatically providing medical information about the filled prescription order, and
automatically updating an inventory of filled prescription orders stored within the pharmacy
wherein associating the unique identifier of the tag with the first and second saved identifiers and automatically detecting the presence of the prescription order are performed by or under control of the computer system.

17. A method of conducting a transaction involving transfer of a filled prescription order from a pharmacy to a customer, the method comprising:
manually depositing a filled prescription order into a storage area for storage;
a computer system automatically detecting removal of the filled prescription order from the storage area; and
upon detecting removal of the filled prescription order from the storage area, the computer system automatically obtaining transaction information to facilitate transfer of the filled prescription order from the pharmacy to the customer.

18. The method of claim 17, wherein automatically obtaining transaction information includes at least one of:
automatically obtaining and populating a form with at least one piece of customer information, the form intended for signature by the customer to signify transfer of the filled prescription order from the pharmacy to the customer,
automatically obtaining a sale price for the filled prescription order, and automatically obtaining medical information about the filled prescription order.

19. The method of claim 17, further comprising, upon detecting removal of the filled prescription order from the storage area, automatically updating an inventory of filled prescription orders stored within the pharmacy.

20. The method of claim 19, wherein automatically updating the inventory includes subtracting the filled prescription order from the inventory of filled prescription orders stored within the pharmacy.

21. The method of claim 20, further comprising automatically updating a global inventory, which records a quantity of items within the pharmacy including items associated with the filled prescription orders stored within the pharmacy, upon subtracting the filled prescription order from the inventory of filled prescription orders stored within the pharmacy.

22. The method of claim 17, further comprising automatically notifying the customer that the filled prescription order is available for transfer from the pharmacy to the customer upon detecting that the filled prescription order is available to be transferred to the customer.

23. The method of claim 17, further comprising receiving a prescription order that becomes the filled prescription order, moving the prescription order along a workflow stream by moving the prescription order by hand between a plurality of physically spaced apart locations to manually fill the prescription order, and automatically tracking the prescription order within the pharmacy as the prescription order moves along the workflow stream to become the filled prescription order.

24. The method of claim 23, wherein automatically tracking the prescription order within the pharmacy includes automatically tracking the prescription order with a tracking system, the tracking system including a tag that is secured for movement with the prescription order, the tracking system also including a tag reader that tracks the location of the tag to thereby track the location of the prescription order, and wherein automatically tracking the prescription order also includes:
- receiving the prescription order at a first location upstream of the storage area;
- operably securing the tag to the prescription order upstream of the storage area, the tag having a unique identifier that is machine-readable by a first location tag reader in proximity to the tag regardless of the orientation of the tag relative to the first tag reader;
- associating the unique identifier of the tag with the first and second saved identifiers in a computer system, the computer system including a computer-readable memory device;
- moving the prescription order by hand to a second location within the pharmacy for manual filling upstream of the storage area, the second location having a second location tag reader in communication with the computer system;
- automatically detecting the presence of the prescription order at the second location by reading the unique identifier of the tag with the second location tag reader regardless of the orientation of the tag and
- automatically recording in the computer system the location of the prescription order at the second location for the manual filling; and
- moving the filled prescription order by hand to the storage area defined by the one of an array of compartments, each compartment having a corresponding compartment tag reader that is in communication with the computer system and is operable to read the unique identifier of the tag on the filled prescription order regardless of the orientation of the tag,
  - wherein associating the unique identifier of the tag with the first and second saved identifiers and automatically detecting the presence of the prescription order are performed by or under control of the computer system.

25. A method of conducting a transaction involving transfer of a filled prescription order from a pharmacy to a customer, the method comprising:
- receiving a prescription order that becomes the filled prescription order;
- moving the prescription order along a workflow stream by moving the prescription order by hand between a plurality of physically spaced apart locations to manually fill the prescription order;
- automatically tracking the prescription order within the pharmacy as the prescription order moves along the workflow stream to become the filled prescription order;
- a computer system automatically detecting that the filled prescription order is available for transfer from the pharmacy to the customer;
- upon detection that the filled prescription order is available for transfer from the pharmacy to the customer, automatically notifying the customer that the filled prescription order is available for transfer from the pharmacy to the customer;
- depositing the filled prescription order into storage;
- receiving a pick-up request for the filled prescription order from the customer;
- detecting removal of the filled prescription order from storage; and
- upon detecting removal of the filled prescription order from storage, performing each of:
- automatically obtaining and populating a form with at least one piece of customer information, the form intended for signature by the customer to signify transfer of the filled prescription order from the pharmacy to the customer,
- automatically providing a sale price for the filled prescription order,
- automatically providing medical information about the filled prescription order, and
- automatically updating an inventory of filled prescription orders stored within the pharmacy.

* * * * *